(12) United States Patent
Kusumegi

(10) Patent No.: US 8,481,294 B2
(45) Date of Patent: Jul. 9, 2013

(54) MUTANT FORMATE DEHYDROGENASE, GENE ENCODING THE SAME, AND METHOD FOR PRODUCING NADH

(75) Inventor: Takahiro Kusumegi, Miyoshi (JP)

(73) Assignee: Toyota Jidosha Kabushiki Kaisha, Aichi (JP)

(*) Notice: Subject to any disclaimer, the term of this patent is extended or adjusted under 35 U.S.C. 154(b) by 0 days.

(21) Appl. No.: 13/388,943

(22) PCT Filed: Aug. 3, 2009

(86) PCT No.: PCT/JP2009/063743
§ 371 (c)(1),
(2), (4) Date: Feb. 3, 2012

(87) PCT Pub. No.: WO2011/016102
PCT Pub. Date: Feb. 10, 2011

(65) Prior Publication Data
US 2012/0129222 A1   May 24, 2012

(51) Int. Cl.
C12P 13/00 (2006.01)
C12Q 1/32 (2006.01)
C07K 1/00 (2006.01)
C07H 21/04 (2006.01)

(52) U.S. Cl.
USPC ............ 435/128; 435/26; 435/189; 536/23.2; 530/350

(58) Field of Classification Search
USPC .................... 435/128, 26; 536/23.2; 530/350
See application file for complete search history.

(56) References Cited

U.S. PATENT DOCUMENTS

| 6,242,234 B1 | 6/2001 | Kula et al. |
| 6,465,396 B1 | 10/2002 | Kobayashi et al. |
| 7,575,909 B2 | 8/2009 | Gupta et al. |
| 2003/0157664 A1 | 8/2003 | Slusarczyk et al. |

FOREIGN PATENT DOCUMENTS

| JP | 63-313580 A | 12/1988 |
| JP | 03-061481 A | 3/1991 |
| JP | 10-023896 A | 1/1998 |
| JP | 11-225784 A | 8/1999 |
| JP | 2000-069971 A | 3/2000 |
| JP | 2000-078970 A | 3/2000 |
| JP | 2000-245471 A | 9/2000 |
| JP | 2002-233395 A | 8/2002 |
| JP | 2003-180383 A | 7/2003 |
| JP | 2003-339390 A | 12/2003 |
| JP | 2004-041062 A | 2/2004 |
| JP | 2007-523617 A | 8/2007 |
| JP | 2009-247296 A | 10/2009 |
| JP | 2010-041971 A | 2/2010 |
| JP | 2010-161983 A | 7/2010 |
| WO | WO 02/46427 A1 | 6/2002 |

OTHER PUBLICATIONS

Alexandra M. Rojkova et al., "Bacterial formate dehydrogenase. Increasing the enzyme thermal stability by hydrophobization of alpha-helices," FEBS Letters, 1999, pp. 183-188, vol. 445.

V.I. Tishkov et al., "Catalytic Mechanism and Application of Formate Dehydrogenase," Biochemistry (Moscow), 2004, pp. 1252-1267, vol. 69, No. 11.

Vladimir I. Tishkov et al., "Protein engineering of formate dehydrogenase," Biomolecular Engineering, 2006, pp. 89-110, vol. 23.

Vladimir O. Popov et al., "NAD+-dependent formate dehydrogenase," Biochem. J., 1994, pp. 625-643, vol. 301.

Primary Examiner — Maryam Monshipouri
(74) Attorney, Agent, or Firm — Sughrue Mion, PLLC

(57) ABSTRACT

Durability of formate dehydrogenase is improved with the use of formate dehydrogenase exhibiting high specific activity that is unpredictable from conventional findings. A specific amino acid substitution is introduced into *Gibberella zeae*-derived formate dehydrogenase. Mutant formate dehydrogenase exhibits durability that is extremely superior to that of wild-type formate dehydrogenase. Thus, the productivity of NADH that is produced using the mutant formate dehydrogenase can be improved.

6 Claims, 17 Drawing Sheets

Fig. 1-1

```
                         1         10                                              20        29
Candida         ---MKIVLVLYDA------GKHAADEE----------------------KLYGCTENKL
C. methylica    ---MKIVLVLYDA------GKHAADEE----------------------KLYGCTENKL
S. cerevisiae   MSKGKVLLVLYEG------GKHAEEQE----------------------KLLGCIENEL
Gibberella      --MVKVLAVLYDG------GQHAKDQP----------------------LLLGTTENEL
Pseudomonas     --MAKVLCVLYDDPVDGYPKTYARDDLPKIDHYPGGQTLPTPKAIDFTPGQLLGSVSGEL
Mycobacterium   --MAKVLCVLYDDPVDGYPKTYARDDLPKIDHYPGGQILPTPKAIDFTPGQLLGSVSGEL
Paracoccus      --MAKVVCVLYDDPVDGYPTSYARDSLPVIERYPDGQTLPTPKAIDFVPGSLLGSVSGEL
                   *::  ***:         :* :.                          * *  ..:*

30        40        50        60        70        80        88
Candida         GIANWLKDQGHELITTSDKEGG-NSVLDQHIPDADIIITTPFHPAYITKERIDKAKKLKL
C. methylica    GIANWLKDQGHELITTSDKEGE-TSELDKHIPDADIIITTPFHPAYITKERLDKAKNLKS
S. cerevisiae   GIRNFIEEQGYELVTTIDKDPEPTSTVDRELKDAEIVITTPFFPAYISRNRIAEAPNLKL
Gibberella      GIRKWLEDQGHTLVTTSDKDRE-GSKFDEELEDAEIIITTPFHPGYLTAERLAKAKKLKL
Pseudomonas     GLRKYLESNGHTLVVTSDKDGP-DSVFERELVDADVVISQPFWPAYLTPERIAKAKNLKL
Mycobacterium   GLREYLESNGHTLVVTSDKDGP-DSVFERELVDADVVISQPFWPAYLTPERIAKAKNLKL
Paracoccus      GLRNYLEAQGHELVVTSSKDGP-DSELEKHLHDAEVVISQPFWPAYLTAERIAKAPKLKL
                *: :::: :*:  *:.* .*:    *.:..: **::*:**  * *.*:: :*: :* :**

89        100       110       120       130       140       148
Candida         VVVAGVGSDHIDLDYINQTGKKISVLEVTGSNVVSVAEHVVMTMLVLVRNFVPAHEQIIN
C. methylica    VVVAGVGSDHIDLDYINQTGKKISVLEVTGSNVVSVAEHVVMTMLVLVRNFVPAHEQIIN
S. cerevisiae   CVTAGVGSDHVDLEAANE--RKITVTEVTGSNVVSVAEHVVMATILVLIRNYNGGHQQAIN
Gibberella      AVTAGIGSDHVDLNAANKTNGGITVAEVTGSNVVSVAEHVLMTILVLIRNFVPAHEQIEA
Pseudomonas     ALTAGIGSDHVDLQSAID--RNVTVAEVTYCNSISVAEHVVMMILSLVRNYLPSHEWARK
Mycobacterium   ALTAGIGSDHVDLQSAID--RNVTVAEVTYCNSISVAEHVVMMILSLVRNYLPSHEWARK
Paracoccus      ALTAGIGSDHVDLQAAID--RGITVAEVTFCNSISVSEHVVMTALNLVRNYTPSHDWAVK
                 :.**:****:**:      ::* *** .* :****:  * *:**   .*:

149       160       170       180       190       200       208
Candida         HDWEVAAIAKDAYDIEGKTIATIGAGRIGYRVLERLVPFNPKELLYYDYQALPKDAEEKV
C. methylica    HDWEVAAIAKDAYDIEGKTIATIGAGRIGYRVLERLLPFNPKELLYYDYQALPKEAEEKV
S. cerevisiae   GEWDIAGVAKNEYDLEDKIISTVGAGRIGYRVLERLVAFNPKKLLYYDYQELPAEAINRL
Gibberella      GEWDVAHAAKQEFDLEGKVVGTVAVGRIGERVLRRLKPFDCKELLYFDYQPLSPEAEKEI
Pseudomonas     GGWNIADCVSHAYDLEAMHVGTVAAGRIGLAVLRRLAPFD-VHLHYTDRHRLPESVEKEL
Mycobacterium   GGWNIADCVSHAYDLEAMHVGTVAAGRIGLAVLRRLAPFD-VHLIYTDRHRLPESVEKEL
Paracoccus      GGWNIADCVTRSYDIEGMHVGTVAAGRIGLAVLRRFKPFG-MHLHYTDRHRLPREVELEL
                 *:*  ..  :*:*  :*.* :.:.****  **::   *  .* * * :  ..   .:
```

Fig. 1-2

```
              209         220        230        240        250    256
Candida       GAR------------RVENIEELVAQADIVTVNAPLHAGTKGLINKELLSKFKKGAWLVN
C.methylica   GAR------------RVENIEELVAQADIVTVNAPLHAGTKGLINKELLSKFKKGAWLVN
S.cerevisiae  NEASKLFNGRGDIVQRVEKLEDMVAQSDVVTINCPLHKDSRGLFNKKLISHMKDGAYLVN
Gibberella    GCR------------RVDTLEEMLAQCDIVTINCPLHEKTKGMFNKDLISKMKKGSYLVN
Pseudomonas   NLT------------WHATREDMYPVCDVVTLNCPLHPETEHMINDETLKLFKRGAYIVN
Mycobacterium NLT------------WHATREDMYPVCDVVTLNCPLHPETEHMINDETLKLFKRGAYIVN
Paracoccus    DLT------------WHESPKDMFPACDVVTLNCPLHPETEHMVNDETLKLFKRGAYLVN
              .         : :: . .*:**:*.***  :. :.*..  :.  :* *:::**

257        270        280        290        300       310    316
Candida       TARGAICVAEDVAAALESGQLRGYGGDVWFPQPAPKDHPWRDMRNKYGAGNAMTPHYSGT
C.methylica   TARGAICVAEDVAAALESGQLRGYGGDVWFPQPAPKDHPWRDMRNKYGAGNAMTPHYSGT
S.cerevisiae  TARGAICVAEDVAEAVKSGKLAGYGGDVWDKQPAPKDHPWRTMDNKDHVGNAMTVHISGT
Gibberella    TARGAIVVKEDVAAALKSGHLAGYGGDVWDHQPAPKEHPLRNAKNNWGGGNAMVPHMSGT
Pseudomonas   TARGKLCDRDAVARALESGRLAGYAGDVWFPQPAPKDHPWRTMPY-----NGMTPHISGT
Mycobacterium TARGKLCDRDAVARALESGRLAGYAGDVWFPQPAPKDHPWRTMPY-----NGMTPHISGT
Paracoccus    TARGKLCDRDAVARALESGQLAGYGGDVWFPQPAPQDHPWRTMPH-----NAMTPHISGT
              ****  :   : ** *::**:* **.****  ****:** *       *.*. * ***

317        330        340        350        360    365
Candida       TLDAQTRYAQGTKNILESFFTGKFDYRPQDIILLNGEYV---TKAYGKHDKK--------
C.methylica   TLDAQTRYAEGTKNILESFFTGKFDYRPQDIILLNGEYV---TKAYGKHDKK--------
S.cerevisiae  SLDAQKRYAQGVKNILNSYFSKKFDYRPQDIIVQNGSYA---TRAYGQKK----------
Gibberella    SLDAQIRYANGTKAIIDSYLSGRHDYNPHDLIVHQGDYA---TKAYGQREKK--------
Pseudomonas   TLTAQARYAAGTREILECFFEGR-PIRDEYLIVQGGALAGTGAHSYSKGNATGGSEEAAK
Mycobacterium TLTAQARYAAGTREILECFFEGR-PIRDEYLIVQGGALAGTGAHSYSKGNATGGSEEAAK
Paracoccus    SLSAQARYAAGTREILECHFEGR-PIRDEYLIVQGGSLAGVGAHSYSKGNATGGSEEAAK
              :* ** *** *.: *::..: :      . .:*: *  .   :::*. : .

Candida       -----
C.methylica   -----
S.cerevisiae  -----
Gibberella    -----
Pseudomonas   FKKAV
Mycobacterium FKKAV
Paracoccus    FKKA-
```

SEQUENCE LISTING

<160> NUMBER OF SEQ ID NOS: 51

<210> SEQ ID NO 1
<211> LENGTH: 1098
<212> TYPE: DNA
<213> ORGANISM: Gibberella zeae
<220> FEATURE:
<221> NAME/KEY: CDS
<222> LOCATION: (1)..(1098)

<400> SEQUENCE: 1

```
atg gtc aag gtt ctt gca gtt ctc tac gac ggt ggc cag cac gcc aag      48
Met Val Lys Val Leu Ala Val Leu Tyr Asp Gly Gly Gln His Ala Lys
1               5                   10                  15 gat caa ccc ctc ctt ctc gga aca act gag aac gag ctc ggc atc cgc      96
Asp Gln Pro Leu Leu Leu Gly Thr Thr Glu Asn Glu Leu Gly Ile Arg
            20                  25                  30 aag tgg ctc gag gac caa ggt cac act ctt gtc acc act tcc gac aag     144
Lys Trp Leu Glu Asp Gln Gly His Thr Leu Val Thr Thr Ser Asp Lys
        35                  40                  45 gac cgt gag ggt tcc aaa ttc gac gag gag ctc gag gat gct gag att     192
Asp Arg Glu Gly Ser Lys Phe Asp Glu Glu Leu Glu Asp Ala Glu Ile
    50                  55                  60 atc atc acc act ccc ttc cac cct ggt tac ctg acc gct gag cgt ctg     240
Ile Ile Thr Thr Pro Phe His Pro Gly Tyr Leu Thr Ala Glu Arg Leu
65                  70                  75                  80 gcc aag gcc aag aag ctc aag ctc gct gtt acc gct ggt atc ggc tcc     288
Ala Lys Ala Lys Lys Leu Lys Leu Ala Val Thr Ala Gly Ile Gly Ser
                85                  90                  95 gac cac gtc gac ctc aac gct gcc aac aag acc aac ggc ggt atc acc     336
Asp His Val Asp Leu Asn Ala Ala Asn Lys Thr Asn Gly Gly Ile Thr
            100                 105                 110 gtt gct gag gtc act ggc tcc aac gtc gtc tct gtt gct gag cac gtt     384
Val Ala Glu Val Thr Gly Ser Asn Val Val Ser Val Ala Glu His Val
        115                 120                 125 ctc atg acc atc ctc gtc ctc atc cgc aac ttc gtc cct gcc cac gag     432
Leu Met Thr Ile Leu Val Leu Ile Arg Asn Phe Val Pro Ala His Glu
    130                 135                 140 cag atc gag gct ggt gag tgg gac gtc gcc cat gct gct aag cag gag     480
Gln Ile Glu Ala Gly Glu Trp Asp Val Ala His Ala Ala Lys Gln Glu
145                 150                 155                 160 ttc gac ctt gag ggc aag gtt gtc ggc act gtc gct gtc ggc cgc atc     528
Phe Asp Leu Glu Gly Lys Val Val Gly Thr Val Ala Val Gly Arg Ile
                165                 170                 175
```

```
ggt gag cgt gtc ctc cgc cgc ctc aag cct ttc gac tgc aag gag ctc     576
Gly Glu Arg Val Leu Arg Arg Leu Lys Pro Phe Asp Cys Lys Glu Leu
        180                 185                 190 ctc tac ttc gac tac cag ccc ctt tcc ccc gag gct gag aag gag atc     624
Leu Tyr Phe Asp Tyr Gln Pro Leu Ser Pro Glu Ala Glu Lys Glu Ile
            195                 200                 205 ggc tgc cgc cgc gtc gac act ctc gag gag atg ctc gct cag tgt gat     672
Gly Cys Arg Arg Val Asp Thr Leu Glu Glu Met Leu Ala Gln Cys Asp
210                 215                 220 att gtc acc atc aac tgc cct ctc cac gag aag acc aag ggt atg ttc     720
Ile Val Thr Ile Asn Cys Pro Leu His Glu Lys Thr Lys Gly Met Phe
225                 230                 235                 240 aac aag gac ctc atc tct aag atg aag aag ggt tct tac ctc gtc aac     768
Asn Lys Asp Leu Ile Ser Lys Met Lys Lys Gly Ser Tyr Leu Val Asn
                245                 250                 255 acc gcc cgt ggc gcc atc gtt gtc aaa gag gac gtc gcc gct gcc ctc     816
Thr Ala Arg Gly Ala Ile Val Val Lys Glu Asp Val Ala Ala Ala Leu
            260                 265                 270 aag tct ggt cac ctc gcc ggt tac ggt ggt gat gtc tgg gac cac cag     864
Lys Ser Gly His Leu Ala Gly Tyr Gly Gly Asp Val Trp Asp His Gln
275                 280                 285 ccc gct ccc aag gag cac cct ctg cga aac gcc aag aac aac tgg ggc     912
Pro Ala Pro Lys Glu His Pro Leu Arg Asn Ala Lys Asn Asn Trp Gly
290                 295                 300 ggt ggt aat gcc atg gtt cct cac atg tct ggt acc tct ctg gat gct     960
Gly Gly Asn Ala Met Val Pro His Met Ser Gly Thr Ser Leu Asp Ala
305                 310                 315                 320 cag atc cga tac gcc aac ggt acc aag gct atc atc gac tct tac ctg    1008
Gln Ile Arg Tyr Ala Asn Gly Thr Lys Ala Ile Ile Asp Ser Tyr Leu
                325                 330                 335 tct ggt cgc cac gac tac aac cct cac gac ctc att gtc cac cag ggt    1056
Ser Gly Arg His Asp Tyr Asn Pro His Asp Leu Ile Val His Gln Gly
            340                 345                 350 gac tac gcc acc aag gct tat ggt cag cgt gag aag aaa tag            1098
Asp Tyr Ala Thr Lys Ala Tyr Gly Gln Arg Glu Lys Lys
                355                 360                 365

<210> SEQ ID NO 2
<211> LENGTH: 365
<212> TYPE: PRT
<213> ORGANISM: Gibberella zeae

<400> SEQUENCE: 2

Met Val Lys Val Leu Ala Val Leu Tyr Asp Gly Gln His Ala Lys
1               5                   10                  15

Asp Gln Pro Leu Leu Leu Gly Thr Thr Glu Asn Glu Leu Gly Ile Arg
            20                  25                  30

Lys Trp Leu Glu Asp Gln Gly His Thr Leu Val Thr Thr Ser Asp Lys
        35                  40                  45

Asp Arg Glu Gly Ser Lys Phe Asp Glu Glu Leu Glu Asp Ala Glu Ile
    50                  55                  60

Ile Ile Thr Thr Pro Phe His Pro Gly Tyr Leu Thr Ala Glu Arg Leu
65                  70                  75                  80

Ala Lys Ala Lys Lys Leu Lys Leu Ala Val Thr Ala Gly Ile Gly Ser
                85                  90                  95

Asp His Val Asp Leu Asn Ala Ala Asn Lys Thr Asn Gly Gly Ile Thr
            100                 105                 110

Val Ala Glu Val Thr Gly Ser Asn Val Val Ser Val Ala Glu His Val
        115                 120                 125
```

```
Leu Met Thr Ile Leu Val Leu Ile Arg Asn Phe Val Pro Ala His Glu
    130                 135                 140

Gln Ile Glu Ala Gly Glu Trp Asp Val Ala His Ala Ala Lys Gln Glu
145                 150                 155                 160

Phe Asp Leu Glu Gly Lys Val Val Gly Thr Val Ala Val Gly Arg Ile
                165                 170                 175

Gly Glu Arg Val Leu Arg Arg Leu Lys Pro Phe Asp Cys Lys Glu Leu
            180                 185                 190

Leu Tyr Phe Asp Tyr Gln Pro Leu Ser Pro Glu Ala Glu Lys Glu Ile
        195                 200                 205

Gly Cys Arg Arg Val Asp Thr Leu Glu Glu Met Leu Ala Gln Cys Asp
    210                 215                 220

Ile Val Thr Ile Asn Cys Pro Leu His Glu Lys Thr Lys Gly Met Phe
225                 230                 235                 240

Asn Lys Asp Leu Ile Ser Lys Met Lys Lys Gly Ser Tyr Leu Val Asn
                245                 250                 255

Thr Ala Arg Gly Ala Ile Val Val Lys Glu Asp Val Ala Ala Ala Leu
            260                 265                 270

Lys Ser Gly His Leu Ala Gly Tyr Gly Gly Asp Val Trp Asp His Gln
        275                 280                 285

Pro Ala Pro Lys Glu His Pro Leu Arg Asn Ala Lys Asn Asn Trp Gly
    290                 295                 300

Gly Gly Asn Ala Met Val Pro His Met Ser Gly Thr Ser Leu Asp Ala
305                 310                 315                 320

Gln Ile Arg Tyr Ala Asn Gly Thr Lys Ala Ile Ile Asp Ser Tyr Leu
                325                 330                 335

Ser Gly Arg His Asp Tyr Asn Pro His Asp Leu Ile Val His Gln Gly
            340                 345                 350

Asp Tyr Ala Thr Lys Ala Tyr Gly Gln Arg Glu Lys Lys
        355                 360                 365

<210> SEQ ID NO 3
<211> LENGTH: 401
<212> TYPE: PRT
<213> ORGANISM: Pseudomonas sp.101

<400> SEQUENCE: 3

Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
                20                  25                  30

Gly Gly Gln Thr Leu Pro Thr Pro Lys Ala Ile Asp Phe Thr Pro Gly
            35                  40                  45

Gln Leu Leu Gly Ser Val Ser Gly Glu Leu Gly Leu Arg Lys Tyr Leu
        50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140
```

```
Tyr Cys Asn Ser Ile Ser Val Ala Glu His Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Asp Arg His
    210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Val

<210> SEQ ID NO 4
<211> LENGTH: 401
<212> TYPE: PRT
<213> ORGANISM: Mycobacterium vaccae N10

<400> SEQUENCE: 4

Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
                20                  25                  30

Gly Gly Gln Ile Leu Pro Thr Pro Lys Ala Ile Asp Phe Thr Pro Gly
            35                  40                  45

Gln Leu Leu Gly Ser Val Ser Gly Glu Leu Gly Leu Arg Glu Tyr Leu
        50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110
```

```
Lys Asn Leu Lys Leu Ala Leu Thr Ala Gly Ile Gly Ser Asp His Val
            115                 120                 125
Asp Leu Gln Ser Ala Ile Asp Arg Asn Val Thr Val Ala Glu Val Thr
        130                 135                 140
Tyr Cys Asn Ser Ile Ser Val Ala Glu His Val Val Met Met Ile Leu
145                 150                 155                 160
Ser Leu Val Arg Asn Tyr Leu Pro Ser His Glu Trp Ala Arg Lys Gly
                165                 170                 175
Gly Trp Asn Ile Ala Asp Cys Val Ser His Ala Tyr Asp Leu Glu Ala
            180                 185                 190
Met His Val Gly Thr Val Ala Ala Gly Arg Ile Gly Leu Ala Val Leu
        195                 200                 205
Arg Arg Leu Ala Pro Phe Asp Val His Leu His Tyr Thr Asp Arg His
210                 215                 220
Arg Leu Pro Glu Ser Val Glu Lys Glu Leu Asn Leu Thr Trp His Ala
225                 230                 235                 240
Thr Arg Glu Asp Met Tyr Pro Val Cys Asp Val Val Thr Leu Asn Cys
                245                 250                 255
Pro Leu His Pro Glu Thr Glu His Met Ile Asn Asp Glu Thr Leu Lys
            260                 265                 270
Leu Phe Lys Arg Gly Ala Tyr Ile Val Asn Thr Ala Arg Gly Lys Leu
        275                 280                 285
Cys Asp Arg Asp Ala Val Ala Arg Ala Leu Glu Ser Gly Arg Leu Ala
290                 295                 300
Gly Tyr Ala Gly Asp Val Trp Phe Pro Gln Pro Ala Pro Lys Asp His
305                 310                 315                 320
Pro Trp Arg Thr Met Pro Tyr Asn Gly Met Thr Pro His Ile Ser Gly
                325                 330                 335
Thr Thr Leu Thr Ala Gln Ala Arg Tyr Ala Ala Gly Thr Arg Glu Ile
            340                 345                 350
Leu Glu Cys Phe Phe Glu Gly Arg Pro Ile Arg Asp Glu Tyr Leu Ile
        355                 360                 365
Val Gln Gly Gly Ala Leu Ala Gly Thr Gly Ala His Ser Tyr Ser Lys
        370                 375                 380
Gly Asn Ala Thr Gly Gly Ser Glu Glu Ala Ala Lys Phe Lys Lys Ala
385                 390                 395                 400
Val

<210> SEQ ID NO 5
<211> LENGTH: 1562
<212> TYPE: DNA
<213> ORGANISM: Candida boidini
<220> FEATURE:
<221> NAME/KEY: CDS
<222> LOCATION: (190)..(1284)

<400> SEQUENCE: 5
ttcaactaaa aattgaacta tttaaacact atgatttcct tcaattatat taaaatcaat      60
ttcatatttc cttacttctt tttgctttat tatacatcaa taactcaatt aactcattga     120
ttatttgaaa aaaaaaaaca tttattaact taactccccg attatatatt atattattga     180 ctttacaaa atg aag atc gtt tta gtc tta tat gat gct ggt aag cac gct    231
           Met Lys Ile Val Leu Val Leu Tyr Asp Ala Gly Lys His Ala
             1               5                  10 gct gat gaa gaa aaa tta tat ggt tgt act gaa aat aaa tta ggt att      279
Ala Asp Glu Glu Lys Leu Tyr Gly Cys Thr Glu Asn Lys Leu Gly Ile
 15                  20                  25                  30
```

```
gct aat tgg tta aaa gat caa ggt cat gaa cta att act act tct gat      327
Ala Asn Trp Leu Lys Asp Gln Gly His Glu Leu Ile Thr Thr Ser Asp
             35                  40                  45 aaa gaa ggt gaa aca agt gaa ttg gat aaa cat atc cca gat gct gat      375
Lys Glu Gly Glu Thr Ser Glu Leu Asp Lys His Ile Pro Asp Ala Asp
         50                  55                  60 att atc atc acc act cct ttc cat cct gct tat atc act aag gaa aga      423
Ile Ile Ile Thr Thr Pro Phe His Pro Ala Tyr Ile Thr Lys Glu Arg
                 65                  70                  75 ctt gac aag gct aag aac tta aaa tta gtc gtt gtc gct ggt gtt ggt      471
Leu Asp Lys Ala Lys Asn Leu Lys Leu Val Val Val Ala Gly Val Gly
             80                  85                  90 tct gat cac att gat tta gat tat att aat caa aca ggt aag aaa atc      519
Ser Asp His Ile Asp Leu Asp Tyr Ile Asn Gln Thr Gly Lys Lys Ile
 95                 100                 105                 110 tca gtc ttg gaa gtt aca ggt tct aat gtt gtc tct gtt gct gaa cac      567
Ser Val Leu Glu Val Thr Gly Ser Asn Val Val Ser Val Ala Glu His
                115                 120                 125 gtt gtc atg acc atg ctt gtc ttg gtt aga aat ttc gtt cca gca cat      615
Val Val Met Thr Met Leu Val Leu Val Arg Asn Phe Val Pro Ala His
            130                 135                 140 gaa caa att att aac cac gat tgg gag gtt gct gct atc gct aag gat      663
Glu Gln Ile Ile Asn His Asp Trp Glu Val Ala Ala Ile Ala Lys Asp
            145                 150                 155 gct tac gat atc gaa ggt aaa act att gct acc att ggt gct ggt aga      711
Ala Tyr Asp Ile Glu Gly Lys Thr Ile Ala Thr Ile Gly Ala Gly Arg
        160                 165                 170 att ggt tac aga gtc ttg gaa aga tta ctc cct ttt aat cca aaa gaa      759
Ile Gly Tyr Arg Val Leu Glu Arg Leu Leu Pro Phe Asn Pro Lys Glu
175                 180                 185                 190 tta tta tac tac gat tat caa gct tta cca aaa gaa gct gaa gaa aaa      807
Leu Leu Tyr Tyr Asp Tyr Gln Ala Leu Pro Lys Glu Ala Glu Glu Lys
                195                 200                 205 gtt ggt gct aga aga gtt gaa aat att gaa gaa tta gtt gct caa gct      855
Val Gly Ala Arg Arg Val Glu Asn Ile Glu Glu Leu Val Ala Gln Ala
            210                 215                 220 gat atc gtt aca gtt aat gct cca tta cac gca ggt aca aaa ggt tta      903
Asp Ile Val Thr Val Asn Ala Pro Leu His Ala Gly Thr Lys Gly Leu
            225                 230                 235 att aat aag gaa tta tta tct aaa ttt aaa aaa ggt gct tgg tta gtc      951
Ile Asn Lys Glu Leu Leu Ser Lys Phe Lys Lys Gly Ala Trp Leu Val
240                 245                 250 aat acc gca aga ggt gct att tgt gtt gct gaa gat gtt gca gca gct      999
Asn Thr Ala Arg Gly Ala Ile Cys Val Ala Glu Asp Val Ala Ala Ala
255                 260                 265                 270 tta gaa tct ggt caa tta aga ggt tac ggt ggt gat gtt tgg ttc cca     1047
Leu Glu Ser Gly Gln Leu Arg Gly Tyr Gly Gly Asp Val Trp Phe Pro
                275                 280                 285 caa cca gct cca aag gat cac cca tgg aga gat atg aga aat aaa tat     1095
Gln Pro Ala Pro Lys Asp His Pro Trp Arg Asp Met Arg Asn Lys Tyr
            290                 295                 300 ggt gct ggt aat gcc atg act cct cac tac tct ggt act act tta gat     1143
Gly Ala Gly Asn Ala Met Thr Pro His Tyr Ser Gly Thr Thr Leu Asp
        305                 310                 315 gct caa aca aga tac gct gaa ggt act aaa aat atc ttg gaa tca ttc     1191
Ala Gln Thr Arg Tyr Ala Glu Gly Thr Lys Asn Ile Leu Glu Ser Phe
320                 325                 330 ttt act ggt aaa ttt gat tac aga cca caa gat att atc tta tta aat     1239
Phe Thr Gly Lys Phe Asp Tyr Arg Pro Gln Asp Ile Ile Leu Leu Asn
335                 340                 345                 350
```

```
ggt gaa tac gtt act aaa gct tac ggt aaa cac gat aag aaa taa      1284
Gly Glu Tyr Val Thr Lys Ala Tyr Gly Lys His Asp Lys Lys
                355                 360 attttcttaa cttgaaaact ataattgcta taacaattct tcaatttctc ttttcttcc  1344 ttttttgaa gaattttaa caatcaaaat tttgactctt tgatttcccg caatctctga   1404
gctcagcata ctcattatta ttttattatt attattata ttactttat tattattata  1464 ttttycttc tttaacgata tcgtttgtgt tttatctttt atgatttaaa ttttatacga  1524
atttatgaat acaacaaaat atttaagttt acacaatg                        1562
```

<210> SEQ ID NO 6
<211> LENGTH: 364
<212> TYPE: PRT
<213> ORGANISM: Candida boidini

<400> SEQUENCE: 6

```
Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
        50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300
```

```
Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
            325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO 7
<211> LENGTH: 1256
<212> TYPE: DNA
<213> ORGANISM: Candida methylica
<220> FEATURE:
<221> NAME/KEY: CDS
<222> LOCATION: (126)..(1220)

<400> SEQUENCE: 7
atatttcctt acttcttttt gctttattat acatcaataa ctcaattaac tcattgatta      60
tttgaaaaaa aaaacattta ttaacttaac accccgatta tatattatat tattaacttt     120 acaaa atg aag atc gtt tta gtc tta tat gat gct ggt aag cac gct gct     170
      Met Lys Ile Val Leu Val Leu Tyr Asp Ala Gly Lys His Ala Ala
       1               5                  10                  15 gat gaa gaa aaa tta tat ggt tgt act gaa aat aaa tta ggt att gct     218
Asp Glu Glu Lys Leu Tyr Gly Cys Thr Glu Asn Lys Leu Gly Ile Ala
             20                  25                  30 aat tgg tta aaa gat caa ggt cat gaa cta att act act tct gat aaa     266
Asn Trp Leu Lys Asp Gln Gly His Glu Leu Ile Thr Thr Ser Asp Lys
         35                  40                  45 gaa ggt gaa aca agt gaa ttg gat aaa cat atc cca gat gct gat att     314
Glu Gly Glu Thr Ser Glu Leu Asp Lys His Ile Pro Asp Ala Asp Ile
     50                  55                  60 atc atc acc act cct ttc cat cct gct tat atc act aag gaa aga ctt     362
Ile Ile Thr Thr Pro Phe His Pro Ala Tyr Ile Thr Lys Glu Arg Leu
 65                  70                  75 gac aag gct aag aac tta aaa tca gtc gtt gtc gct ggt gtt ggt tct     410
Asp Lys Ala Lys Asn Leu Lys Ser Val Val Val Ala Gly Val Gly Ser
 80                  85                  90                  95 gat cac att gat tta gat tat att aat caa aca ggt aag aaa atc tca     458
Asp His Ile Asp Leu Asp Tyr Ile Asn Gln Thr Gly Lys Lys Ile Ser
                100                 105                 110 gtc ctg gaa gtt aca ggt tct aat gtt gtc tct gtt gct gaa cac gtt     506
Val Leu Glu Val Thr Gly Ser Asn Val Val Ser Val Ala Glu His Val
            115                 120                 125 gtc atg acc atg ctt gtc ttg gtt aga aat ttc gtt cca gca cat gaa     554
Val Met Thr Met Leu Val Leu Val Arg Asn Phe Val Pro Ala His Glu
        130                 135                 140 caa att att aac cac gat tgg gag gtt gct gct atc gct aag gat gct     602
Gln Ile Ile Asn His Asp Trp Glu Val Ala Ala Ile Ala Lys Asp Ala
    145                 150                 155 tac gat atc gaa ggt aaa act atc gct acc att ggt gct ggt aga att     650
Tyr Asp Ile Glu Gly Lys Thr Ile Ala Thr Ile Gly Ala Gly Arg Ile
160                 165                 170                 175 ggt tac aga gtc ttg gaa aga tta ctc cca ttt aat cca aaa gaa tta     698
Gly Tyr Arg Val Leu Glu Arg Leu Leu Pro Phe Asn Pro Lys Glu Leu
                180                 185                 190 tta tac tac gat tat caa gct tta cca aaa gaa gct gaa gaa aaa gtt     746
Leu Tyr Tyr Asp Tyr Gln Ala Leu Pro Lys Glu Ala Glu Glu Lys Val
            195                 200                 205 ggt gct aga aga gtt gaa aat att gaa gaa tta gtt gct caa gct gat     794
Gly Ala Arg Arg Val Glu Asn Ile Glu Glu Leu Val Ala Gln Ala Asp
```

```
Gly Ala Arg Arg Val Glu Asn Ile Glu Glu Leu Val Ala Gln Ala Asp
            210                 215                 220 atc gtt aca gtt aat gct cca tta cac gca ggt aca aaa ggt tta att      842
Ile Val Thr Val Asn Ala Pro Leu His Ala Gly Thr Lys Gly Leu Ile
        225                 230                 235 aat aag gaa tta tta tct aaa ttt aaa aaa ggt gct tgg tta gtc aat      890
Asn Lys Glu Leu Leu Ser Lys Phe Lys Lys Gly Ala Trp Leu Val Asn
240                 245                 250                 255 acc gca aga ggt gct att tgt gtt gct gaa gat gtt gca gca gct tta      938
Thr Ala Arg Gly Ala Ile Cys Val Ala Glu Asp Val Ala Ala Ala Leu
                260                 265                 270 gaa tct ggt caa tta aga ggt tac ggt ggt gat gtt tgg ttc cca caa      986
Glu Ser Gly Gln Leu Arg Gly Tyr Gly Gly Asp Val Trp Phe Pro Gln
            275                 280                 285 cca gct cca aag gat cac cca tgg aga gat atg aga aat aaa tat ggt     1034
Pro Ala Pro Lys Asp His Pro Trp Arg Asp Met Arg Asn Lys Tyr Gly
        290                 295                 300 gct ggt aat gcc atg act cct cac tac tct ggt act act tta gac gct     1082
Ala Gly Asn Ala Met Thr Pro His Tyr Ser Gly Thr Thr Leu Asp Ala
305                 310                 315 caa aca aga tac gct gaa ggt act aaa aat att ttg gaa tca ttc ttt     1130
Gln Thr Arg Tyr Ala Glu Gly Thr Lys Asn Ile Leu Glu Ser Phe Phe
320                 325                 330                 335 acc ggt aaa ttt gat tac aga cca caa gat att atc tta tta aat ggt     1178
Thr Gly Lys Phe Asp Tyr Arg Pro Gln Asp Ile Ile Leu Leu Asn Gly
                340                 345                 350 gaa tac gtt act aaa gct tac ggt aaa cac gat aag aaa taa             1220
Glu Tyr Val Thr Lys Ala Tyr Gly Lys His Asp Lys Lys
            355                 360 attttcttaa cttgaaaact ataatygcta taacaa                             1256

<210> SEQ ID NO 8
<211> LENGTH: 364
<212> TYPE: PRT
<213> ORGANISM: Candida methylica

<400> SEQUENCE: 8

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Ser Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
```

```
                        165                 170                 175
Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO 9
<211> LENGTH: 1131
<212> TYPE: DNA
<213> ORGANISM: Saccharomyces cerevisiae
<220> FEATURE:
<221> NAME/KEY: CDS
<222> LOCATION: (1)..(1131)

<400> SEQUENCE: 9 atg tcg aag gga aag gtt ttg ctg gtt ctt tac gaa ggt ggt aag cat    48
Met Ser Lys Gly Lys Val Leu Leu Val Leu Tyr Glu Gly Gly Lys His
1               5                   10                  15 gct gaa gag cag gaa aag tta ttg ggg tgt att gaa aat gaa ctt ggt    96
Ala Glu Glu Gln Glu Lys Leu Leu Gly Cys Ile Glu Asn Glu Leu Gly
                20                  25                  30 atc aga aat ttc att gaa gaa cag gga tac gag ttg gtt act acc att   144
Ile Arg Asn Phe Ile Glu Glu Gln Gly Tyr Glu Leu Val Thr Thr Ile
            35                  40                  45 gac aag gac cct gag cca acc tca acg gta gac agg gag ttg aaa gac   192
Asp Lys Asp Pro Glu Pro Thr Ser Thr Val Asp Arg Glu Leu Lys Asp
        50                  55                  60 gct gaa att gtc att act acg ccc ttt ttc ccc gcc tac atc tcg aga   240
Ala Glu Ile Val Ile Thr Thr Pro Phe Phe Pro Ala Tyr Ile Ser Arg
65                  70                  75                  80 aac agg att gca gaa gct cct aac ctg aag ctc tgt gta acc gct ggc   288
Asn Arg Ile Ala Glu Ala Pro Asn Leu Lys Leu Cys Val Thr Ala Gly
                85                  90                  95 gtc ggt tca gac cat gtc gat tta gaa gct gca aat gaa cgg aaa atc   336
Val Gly Ser Asp His Val Asp Leu Glu Ala Ala Asn Glu Arg Lys Ile
            100                 105                 110 acg gtc acc gaa gtt act ggt tct aac gtc gtt tct gtc gca gag cac   384
Thr Val Thr Glu Val Thr Gly Ser Asn Val Val Ser Val Ala Glu His
        115                 120                 125
```

```
gtt atg gcc aca att ttg gtt ttg ata aga aac tat aat ggt ggt cat      432
Val Met Ala Thr Ile Leu Val Leu Ile Arg Asn Tyr Asn Gly Gly His
    130                 135                 140 caa caa gca att aat ggt gag tgg gat att gcc ggc gtg gct aaa aat      480
Gln Gln Ala Ile Asn Gly Glu Trp Asp Ile Ala Gly Val Ala Lys Asn
145                 150                 155                 160 gag tat gat ctg gaa gac aaa ata att tca acg gta ggt gcc ggt aga      528
Glu Tyr Asp Leu Glu Asp Lys Ile Ile Ser Thr Val Gly Ala Gly Arg
                165                 170                 175 att gga tat agg gtt ctg gaa aga ttg gtc gca ttt aat ccg aag aag      576
Ile Gly Tyr Arg Val Leu Glu Arg Leu Val Ala Phe Asn Pro Lys Lys
            180                 185                 190 tta ctg tac tac gac tac cag gaa cta cct gcg gaa gca atc aat aga      624
Leu Leu Tyr Tyr Asp Tyr Gln Glu Leu Pro Ala Glu Ala Ile Asn Arg
        195                 200                 205 ttg aac gag gcc agc aag ctt ttc aat ggc aga ggt gat att gtt cag      672
Leu Asn Glu Ala Ser Lys Leu Phe Asn Gly Arg Gly Asp Ile Val Gln
    210                 215                 220 aga gta gag aaa ttg gag gat atg gtt gct cag tca gat gtt gtt acc      720
Arg Val Glu Lys Leu Glu Asp Met Val Ala Gln Ser Asp Val Val Thr
225                 230                 235                 240 atc aac tgt cca ttg cac aag gac tca agg ggt tta ttc aat aaa aag      768
Ile Asn Cys Pro Leu His Lys Asp Ser Arg Gly Leu Phe Asn Lys Lys
                245                 250                 255 ctt att tcc cac atg aaa gat ggt gca tac ttg gtg aat acc gct aga      816
Leu Ile Ser His Met Lys Asp Gly Ala Tyr Leu Val Asn Thr Ala Arg
            260                 265                 270 ggt gct att tgt gtc gca gaa gat gtt gcc gag gca gtc aag tct ggt      864
Gly Ala Ile Cys Val Ala Glu Asp Val Ala Glu Ala Val Lys Ser Gly
        275                 280                 285 aaa ttg gct ggc tat ggt ggt gat gtc tgg gat aag caa cca gca cca      912
Lys Leu Ala Gly Tyr Gly Gly Asp Val Trp Asp Lys Gln Pro Ala Pro
    290                 295                 300 aaa gac cat ccc tgg agg act atg gac aat aag gac cac gtg gga aac      960
Lys Asp His Pro Trp Arg Thr Met Asp Asn Lys Asp His Val Gly Asn
305                 310                 315                 320 gca atg act gtt cat atc agt ggc aca tct ctg gat gct caa aag agg     1008
Ala Met Thr Val His Ile Ser Gly Thr Ser Leu Asp Ala Gln Lys Arg
                325                 330                 335 tac gct cag gga gta aag aac atc cta aat agt tac ttt tcc aaa aag     1056
Tyr Ala Gln Gly Val Lys Asn Ile Leu Asn Ser Tyr Phe Ser Lys Lys
            340                 345                 350 ttt gat tac cgt cca cag gat att att gtg cag aat ggt tct tat gcc     1104
Phe Asp Tyr Arg Pro Gln Asp Ile Ile Val Gln Asn Gly Ser Tyr Ala
        355                 360                 365 acc aga gct tat gga cag aag aaa taa                                  1131
Thr Arg Ala Tyr Gly Gln Lys Lys
    370                 375

<210> SEQ ID NO 10
<211> LENGTH: 376
<212> TYPE: PRT
<213> ORGANISM: Saccharomyces cerevisiae

<400> SEQUENCE: 10

Met Ser Lys Gly Lys Val Leu Leu Val Leu Tyr Glu Gly Gly Lys His
1               5                   10                  15

Ala Glu Gln Glu Lys Leu Leu Gly Cys Ile Glu Asn Glu Leu Gly
            20                  25                  30

Ile Arg Asn Phe Ile Glu Glu Gln Gly Tyr Glu Leu Val Thr Thr Ile
```

```
                35                  40                  45
Asp Lys Asp Pro Glu Pro Thr Ser Thr Val Asp Arg Glu Leu Lys Asp
 50                  55                  60

Ala Glu Ile Val Ile Thr Thr Pro Phe Phe Pro Ala Tyr Ile Ser Arg
 65                  70                  75                  80

Asn Arg Ile Ala Glu Ala Pro Asn Leu Lys Leu Cys Val Thr Ala Gly
                 85                  90                  95

Val Gly Ser Asp His Val Asp Leu Glu Ala Ala Asn Glu Arg Lys Ile
            100                 105                 110

Thr Val Thr Glu Val Thr Gly Ser Asn Val Val Ser Val Ala Glu His
        115                 120                 125

Val Met Ala Thr Ile Leu Val Leu Ile Arg Asn Tyr Asn Gly Gly His
130                 135                 140

Gln Gln Ala Ile Asn Gly Glu Trp Asp Ile Ala Gly Val Ala Lys Asn
145                 150                 155                 160

Glu Tyr Asp Leu Glu Asp Lys Ile Ile Ser Thr Val Gly Ala Gly Arg
                165                 170                 175

Ile Gly Tyr Arg Val Leu Glu Arg Leu Val Ala Phe Asn Pro Lys Lys
            180                 185                 190

Leu Leu Tyr Tyr Asp Tyr Gln Glu Leu Pro Ala Glu Ala Ile Asn Arg
        195                 200                 205

Leu Asn Glu Ala Ser Lys Leu Phe Asn Gly Arg Gly Asp Ile Val Gln
210                 215                 220

Arg Val Glu Lys Leu Glu Asp Met Val Ala Gln Ser Asp Val Val Thr
225                 230                 235                 240

Ile Asn Cys Pro Leu His Lys Asp Ser Arg Gly Leu Phe Asn Lys Lys
                245                 250                 255

Leu Ile Ser His Met Lys Asp Gly Ala Tyr Leu Val Asn Thr Ala Arg
            260                 265                 270

Gly Ala Ile Cys Val Ala Glu Asp Val Ala Glu Ala Val Lys Ser Gly
        275                 280                 285

Lys Leu Ala Gly Tyr Gly Gly Asp Val Trp Asp Lys Gln Pro Ala Pro
290                 295                 300

Lys Asp His Pro Trp Arg Thr Met Asp Asn Lys Asp His Val Gly Asn
305                 310                 315                 320

Ala Met Thr Val His Ile Ser Gly Thr Ser Leu Asp Ala Gln Lys Arg
                325                 330                 335

Tyr Ala Gln Gly Val Lys Asn Ile Leu Asn Ser Tyr Phe Ser Lys Lys
            340                 345                 350

Phe Asp Tyr Arg Pro Gln Asp Ile Ile Val Gln Asn Gly Ser Tyr Ala
        355                 360                 365

Thr Arg Ala Tyr Gly Gln Lys Lys
370                 375

<210> SEQ ID NO 11
<211> LENGTH: 1455
<212> TYPE: DNA
<213> ORGANISM: Paracoccus sp.12-A
<220> FEATURE:
<221> NAME/KEY: CDS
<222> LOCATION: (231)..(1433)

<400> SEQUENCE: 11
gatcgttgaa aaactccgat ttgcggatgc ggccacgggc gggcagggtt gccctgtcca      60
cgagacacct cgcacaaacc gaggcatcca gggaggaaag ccccgacatc gcgcggcatc     120
```

-continued

```
gccggtccgc ctgcccgatg gtgccatcgg gacaggcctg cggttccgca tgcccgacga        180
cggcgcgcgg agggggcttc tggctgccgc atgaaccgaa aggaagactt atg gcc          236
                                                       Met Ala
                                                         1 aag gta gtt tgc gtt ctt tac gac gat ccg gtc gac ggc tat ccg acc        284
Lys Val Val Cys Val Leu Tyr Asp Asp Pro Val Asp Gly Tyr Pro Thr
      5               10                  15 tct tac gcc cgc gat tcc ctg ccg gtg atc gag cgc tat ccc gac ggg        332
Ser Tyr Ala Arg Asp Ser Leu Pro Val Ile Glu Arg Tyr Pro Asp Gly
 20                  25                  30 cag acc ctg ccc acg ccc aag gcc atc gac ttc gtg ccg ggc agc ctg        380
Gln Thr Leu Pro Thr Pro Lys Ala Ile Asp Phe Val Pro Gly Ser Leu
 35                  40                  45                  50 ctc ggt tcg gtc tcg ggc gag ctg ggc ctg cgc aac tac ctg gaa gcg        428
Leu Gly Ser Val Ser Gly Glu Leu Gly Leu Arg Asn Tyr Leu Glu Ala
                 55                  60                  65 cag ggc cac gaa ctg gtg gtg acc tcg tcc aag gac ggc ccc gac agc        476
Gln Gly His Glu Leu Val Val Thr Ser Ser Lys Asp Gly Pro Asp Ser
                 70                  75                  80 gag ctg gaa aag cac ctg cac gat gcc gag gtg gtc atc tcg cag ccg        524
Glu Leu Glu Lys His Leu His Asp Ala Glu Val Val Ile Ser Gln Pro
                 85                  90                  95 ttc tgg ccg gcc tat ctg acc gcc gag cgc atc gcc aag gcg ccg aag        572
Phe Trp Pro Ala Tyr Leu Thr Ala Glu Arg Ile Ala Lys Ala Pro Lys
100                 105                 110 ctg aag ctg gcg ctg acc gcc ggc atc ggc tcg gac cat gtc gac ctg        620
Leu Lys Leu Ala Leu Thr Ala Gly Ile Gly Ser Asp His Val Asp Leu
115                 120                 125                 130 caa gcg gcc atc gac cgc ggc atc acc gtg gcc gag gtg acc ttc tgc        668
Gln Ala Ala Ile Asp Arg Gly Ile Thr Val Ala Glu Val Thr Phe Cys
                135                 140                 145 aac tcg atc agc gtg tcg gaa cat gtg gtg atg acg gcg ctg aac ctg        716
Asn Ser Ile Ser Val Ser Glu His Val Val Met Thr Ala Leu Asn Leu
                150                 155                 160 gtg cgg aac tac acc ccc tcg cat gac tgg gcg gtg aag ggc ggc tgg        764
Val Arg Asn Tyr Thr Pro Ser His Asp Trp Ala Val Lys Gly Gly Trp
                165                 170                 175 aac atc gcc gat tgc gtc acc cgt tcc tat gac atc gag ggg atg cat        812
Asn Ile Ala Asp Cys Val Thr Arg Ser Tyr Asp Ile Glu Gly Met His
180                 185                 190 gtc ggc acc gtc gcc gcc ggc cgc atc ggc ctg gcg gtg ctg cgc cgc        860
Val Gly Thr Val Ala Ala Gly Arg Ile Gly Leu Ala Val Leu Arg Arg
195                 200                 205                 210 ttc aag ccc ttc ggc atg cac ctg cac tat acc gac cgc cac cgc ctg        908
Phe Lys Pro Phe Gly Met His Leu His Tyr Thr Asp Arg His Arg Leu
                215                 220                 225 ccg cgc gag gtc gaa ctg gag ctg gac ctg acc tgg cac gag agc ccc        956
Pro Arg Glu Val Glu Leu Glu Leu Asp Leu Thr Trp His Glu Ser Pro
                230                 235                 240 aag gac atg ttc ccg gcc tgc gac gtc gtc acg ctg aac tgc ccg ctg       1004
Lys Asp Met Phe Pro Ala Cys Asp Val Val Thr Leu Asn Cys Pro Leu
                245                 250                 255 cac ccc gag acc gag cat atg gtc aac gac gag acg ctg aag ctg ttc       1052
His Pro Glu Thr Glu His Met Val Asn Asp Glu Thr Leu Lys Leu Phe
260                 265                 270 aag cgc ggc gcc tat ctg gtc aac acg gcg cgc ggc aag ctg tgc gac       1100
Lys Arg Gly Ala Tyr Leu Val Asn Thr Ala Arg Gly Lys Leu Cys Asp
275                 280                 285                 290 cgc gat gcg gtg gcc cgc gcg ctg gag agc ggc cag ctg gcc ggc tat       1148
Arg Asp Ala Val Ala Arg Ala Leu Glu Ser Gly Gln Leu Ala Gly Tyr
```

```
                           295                     300                     305
ggc ggc gac gtc tgg ttc ccg cag ccg gcg ccg cag gac cat ccc tgg            1196
Gly Gly Asp Val Trp Phe Pro Gln Pro Ala Pro Gln Asp His Pro Trp
            310                     315                     320 cgc acc atg ccg cat aac gcg atg acg ccg cat atc tcg ggc acc tcg            1244
Arg Thr Met Pro His Asn Ala Met Thr Pro His Ile Ser Gly Thr Ser
        325                     330                     335 ctg tcg gcg cag gcg cgc tat gcg gcc ggc acg cgc gag atc ctc gaa            1292
Leu Ser Ala Gln Ala Arg Tyr Ala Ala Gly Thr Arg Glu Ile Leu Glu
    340                     345                     350 tgc cat ttc gag ggc cga ccg atc cgc gac gaa tat ctg atc gtg cag            1340
Cys His Phe Glu Gly Arg Pro Ile Arg Asp Glu Tyr Leu Ile Val Gln
355                     360                     365                     370 ggc ggc agc ctg gcc ggc gtc ggc gcg cat tcc tat tcc aag ggc aat            1388
Gly Gly Ser Leu Ala Gly Val Gly Ala His Ser Tyr Ser Lys Gly Asn
                375                     380                     385 gcc acc ggc ggc tcg gaa gag gcg gcg aag ttc aag aag gcc tga                1433
Ala Thr Gly Gly Ser Glu Glu Ala Ala Lys Phe Lys Lys Ala
            390                     395                     400 tcgagaaaac cggccctcgc ga                                                   1455

<210> SEQ ID NO 12
<211> LENGTH: 400
<212> TYPE: PRT
<213> ORGANISM: Paracoccus sp.12-A

<400> SEQUENCE: 12

Met Ala Lys Val Val Cys Val Leu Tyr Asp Asp Pro Val Asp Gly Tyr
1               5                   10                  15

Pro Thr Ser Tyr Ala Arg Asp Ser Leu Pro Val Ile Glu Arg Tyr Pro
            20                  25                  30

Asp Gly Gln Thr Leu Pro Thr Pro Lys Ala Ile Asp Phe Val Pro Gly
        35                  40                  45

Ser Leu Leu Gly Ser Val Ser Gly Glu Leu Gly Leu Arg Asn Tyr Leu
    50                  55                  60

Glu Ala Gln Gly His Glu Leu Val Val Thr Ser Ser Lys Asp Gly Pro
65                  70                  75                  80

Asp Ser Glu Leu Glu Lys His Leu His Asp Ala Glu Val Val Ile Ser
                85                  90                  95

Gln Pro Phe Trp Pro Ala Tyr Leu Thr Ala Glu Arg Ile Ala Lys Ala
            100                 105                 110

Pro Lys Leu Lys Leu Ala Leu Thr Ala Gly Ile Gly Ser Asp His Val
        115                 120                 125

Asp Leu Gln Ala Ala Ile Asp Arg Gly Ile Thr Val Ala Glu Val Thr
    130                 135                 140

Phe Cys Asn Ser Ile Ser Val Ser Glu His Val Val Met Thr Ala Leu
145                 150                 155                 160

Asn Leu Val Arg Asn Tyr Thr Pro Ser His Asp Trp Ala Val Lys Gly
                165                 170                 175

Gly Trp Asn Ile Ala Asp Cys Val Thr Arg Ser Tyr Asp Ile Glu Gly
            180                 185                 190

Met His Val Gly Thr Val Ala Ala Gly Arg Ile Gly Leu Ala Val Leu
        195                 200                 205

Arg Arg Phe Lys Pro Phe Gly Met His Leu His Tyr Thr Asp Arg His
    210                 215                 220

Arg Leu Pro Arg Glu Val Glu Leu Glu Leu Asp Leu Thr Trp His Glu
225                 230                 235                 240
```

-continued

```
Ser Pro Lys Asp Met Phe Pro Ala Cys Asp Val Val Thr Leu Asn Cys
            245                 250                 255

Pro Leu His Pro Glu Thr Glu His Met Val Asn Asp Glu Thr Leu Lys
        260                 265                 270

Leu Phe Lys Arg Gly Ala Tyr Leu Val Asn Thr Ala Arg Gly Lys Leu
    275                 280                 285

Cys Asp Arg Asp Ala Val Ala Arg Ala Leu Glu Ser Gly Gln Leu Ala
290                 295                 300

Gly Tyr Gly Gly Asp Val Trp Phe Pro Gln Pro Ala Pro Gln Asp His
305                 310                 315                 320

Pro Trp Arg Thr Met Pro His Asn Ala Met Thr Pro His Ile Ser Gly
                325                 330                 335

Thr Ser Leu Ser Ala Gln Ala Arg Tyr Ala Ala Gly Thr Arg Glu Ile
            340                 345                 350

Leu Glu Cys His Phe Glu Gly Arg Pro Ile Arg Asp Glu Tyr Leu Ile
        355                 360                 365

Val Gln Gly Gly Ser Leu Ala Gly Val Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

<210> SEQ ID NO 13
<211> LENGTH: 28
<212> TYPE: DNA
<213> ORGANISM: Artificial Sequence
<220> FEATURE:
<223> OTHER INFORMATION: Synthetic DNA

<400> SEQUENCE: 13
cgccatatgg tcaaggttct tgcagttc                                        28

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
ctatttcttc tcacgctgac c                                               21

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15
tacgccaaga acaactgggg c                                               21

<210> SEQ ID NO 16
<211> LENGTH: 22
<212> TYPE: DNA
<213> ORGANISM: Artificial Sequence
<220> FEATURE:
<223> OTHER INFORMATION: Synthetic DNA

<400> SEQUENCE: 16
tcgcagaggg tgctccttgg ga                                              22
```

```
<210> SEQ ID NO 17
<211> LENGTH: 23
<212> TYPE: DNA
<213> ORGANISM: Artificial Sequence
<220> FEATURE:
<223> OTHER INFORMATION: Synthetic DNA

<400> SEQUENCE: 17
cttacctgac cgctgagcgt ctg                                    23

<210> SEQ ID NO 18
<211> LENGTH: 22
<212> TYPE: DNA
<213> ORGANISM: Artificial Sequence
<220> FEATURE:
<223> OTHER INFORMATION: Synthetic DNA

<400> SEQUENCE: 18
cagggtggaa gggagtggtg at                                     22

<210> SEQ ID NO 19
<211> LENGTH: 23
<212> TYPE: DNA
<213> ORGANISM: Artificial Sequence
<220> FEATURE:
<223> OTHER INFORMATION: Synthetic DNA

<400> SEQUENCE: 19
aaagctgcta agcaggagtt cga                                    23

<210> SEQ ID NO 20
<211> LENGTH: 23
<212> TYPE: DNA
<213> ORGANISM: Artificial Sequence
<220> FEATURE:
<223> OTHER INFORMATION: Synthetic DNA

<400> SEQUENCE: 20
ggcgatgtcc cactcaccag cct                                    23

<210> SEQ ID NO 21
<211> LENGTH: 26
<212> TYPE: DNA
<213> ORGANISM: Artificial Sequence
<220> FEATURE:
<223> OTHER INFORMATION: Synthetic DNA

<400> SEQUENCE: 21
ttgttcaaca aggacctcat ctccaa                                 26

<210> SEQ ID NO 22
<211> LENGTH: 23
<212> TYPE: DNA
<213> ORGANISM: Artificial Sequence
<220> FEATURE:
<223> OTHER INFORMATION: Synthetic DNA

<400> SEQUENCE: 22
acccttggtc ttctcgtgga gag                                    23

<210> SEQ ID NO 23
<211> LENGTH: 26
<212> TYPE: DNA
<213> ORGANISM: Artificial Sequence
<220> FEATURE:
<223> OTHER INFORMATION: Synthetic DNA

<400> SEQUENCE: 23
```
gacccacagc ccgctcccaa ggagca                                      26

<210> SEQ ID NO 24
<211> LENGTH: 26
<212> TYPE: DNA
<213> ORGANISM: Artificial Sequence
<220> FEATURE:
<223> OTHER INFORMATION: Synthetic DNA

<400> SEQUENCE: 24
ccagacatca ccaccgtaac cggcga                                      26

<210> SEQ ID NO 25
<211> LENGTH: 24
<212> TYPE: DNA
<213> ORGANISM: Artificial Sequence
<220> FEATURE:
<223> OTHER INFORMATION: Synthetic DNA

<400> SEQUENCE: 25
ctccgcaagt ggctcgagga ccaa                                        24

<210> SEQ ID NO 26
<211> LENGTH: 22
<212> TYPE: DNA
<213> ORGANISM: Artificial Sequence
<220> FEATURE:
<223> OTHER INFORMATION: Synthetic DNA

<400> SEQUENCE: 26
gccgagctcg ttctcagttg tt                                          22

<210> SEQ ID NO 27
<211> LENGTH: 23
<212> TYPE: DNA
<213> ORGANISM: Artificial Sequence
<220> FEATURE:
<223> OTHER INFORMATION: Synthetic DNA

<400> SEQUENCE: 27
ggtgagggtt ccaaattcga cga                                         23

<210> SEQ ID NO 28
<211> LENGTH: 20
<212> TYPE: DNA
<213> ORGANISM: Artificial Sequence
<220> FEATURE:
<223> OTHER INFORMATION: Synthetic DNA

<400> SEQUENCE: 28
gtccttgtcg gaagtggtga                                             20

<210> SEQ ID NO 29
<211> LENGTH: 23
<212> TYPE: DNA
<213> ORGANISM: Artificial Sequence
<220> FEATURE:
<223> OTHER INFORMATION: Synthetic DNA

<400> SEQUENCE: 29
gtccgcaact tcgtccctgc cca                                         23

<210> SEQ ID NO 30
<211> LENGTH: 22
<212> TYPE: DNA
<213> ORGANISM: Artificial Sequence

```
<220> FEATURE:
<223> OTHER INFORMATION: Synthetic DNA

<400> SEQUENCE: 30
gaggacgagg atggtcatga ga                                              22

<210> SEQ ID NO 31
<211> LENGTH: 23
<212> TYPE: DNA
<213> ORGANISM: Artificial Sequence
<220> FEATURE:
<223> OTHER INFORMATION: Synthetic DNA

<400> SEQUENCE: 31
tcaccctctg cgatacgcca aga                                             23

<210> SEQ ID NO 32
<211> LENGTH: 22
<212> TYPE: DNA
<213> ORGANISM: Artificial Sequence
<220> FEATURE:
<223> OTHER INFORMATION: Synthetic DNA

<400> SEQUENCE: 32
tccttgggag cgggctggtg gt                                              22

<210> SEQ ID NO 33
<211> LENGTH: 25
<212> TYPE: DNA
<213> ORGANISM: Artificial Sequence
<220> FEATURE:
<223> OTHER INFORMATION: Synthetic DNA

<400> SEQUENCE: 33
gacctcacga cctcattgtc cacca                                           25

<210> SEQ ID NO 34
<211> LENGTH: 24
<212> TYPE: DNA
<213> ORGANISM: Artificial Sequence
<220> FEATURE:
<223> OTHER INFORMATION: Synthetic DNA

<400> SEQUENCE: 34
tgtagtcgtg gcgaccagac aggt                                            24

<210> SEQ ID NO 35
<211> LENGTH: 23
<212> TYPE: DNA
<213> ORGANISM: Artificial Sequence
<220> FEATURE:
<223> OTHER INFORMATION: Synthetic DNA

<400> SEQUENCE: 35
gtcatcatca ccactccctt cca                                             23

<210> SEQ ID NO 36
<211> LENGTH: 20
<212> TYPE: DNA
<213> ORGANISM: Artificial Sequence
<220> FEATURE:
<223> OTHER INFORMATION: Synthetic DNA

<400> SEQUENCE: 36
ctcagcatcc tcgagctcct                                                 20
```

```
<210> SEQ ID NO 37
<211> LENGTH: 23
<212> TYPE: DNA
<213> ORGANISM: Artificial Sequence
<220> FEATURE:
<223> OTHER INFORMATION: Synthetic DNA

<400> SEQUENCE: 37
gggccaagaa gctcaagctc gct                                              23

<210> SEQ ID NO 38
<211> LENGTH: 21
<212> TYPE: DNA
<213> ORGANISM: Artificial Sequence
<220> FEATURE:
<223> OTHER INFORMATION: Synthetic DNA

<400> SEQUENCE: 38
tggccagacg ctcagcggtc a                                                21

<210> SEQ ID NO 39
<211> LENGTH: 29
<212> TYPE: DNA
<213> ORGANISM: Artificial Sequence
<220> FEATURE:
<223> OTHER INFORMATION: Synthetic DNA

<400> SEQUENCE: 39
aaagcggcta agctggagtt cgaccttga                                        29

<210> SEQ ID NO 40
<211> LENGTH: 26
<212> TYPE: DNA
<213> ORGANISM: Artificial Sequence
<220> FEATURE:
<223> OTHER INFORMATION: Synthetic DNA

<400> SEQUENCE: 40
atcgacctca acgctgccaa caagac                                           26

<210> SEQ ID NO 41
<211> LENGTH: 25
<212> TYPE: DNA
<213> ORGANISM: Artificial Sequence
<220> FEATURE:
<223> OTHER INFORMATION: Synthetic DNA

<400> SEQUENCE: 41
gtggtcggag ccgataccag cggta                                            25

<210> SEQ ID NO 42
<211> LENGTH: 28
<212> TYPE: DNA
<213> ORGANISM: Artificial Sequence
<220> FEATURE:
<223> OTHER INFORMATION: Synthetic DNA

<400> SEQUENCE: 42
agctgctaag caggagttcg accttgag                                         28

<210> SEQ ID NO 43
<211> LENGTH: 21
<212> TYPE: DNA
<213> ORGANISM: Artificial Sequence
<220> FEATURE:
<223> OTHER INFORMATION: Synthetic DNA

<400> SEQUENCE: 43
```

```
acagcccgct cccaaggagc a                                            21

<210> SEQ ID NO 44
<211> LENGTH: 22
<212> TYPE: DNA
<213> ORGANISM: Artificial Sequence
<220> FEATURE:
<223> OTHER INFORMATION: Synthetic DNA

<400> SEQUENCE: 44
tggtcccaga catcaccacc gt                                           22

<210> SEQ ID NO 45
<211> LENGTH: 24
<212> TYPE: DNA
<213> ORGANISM: Artificial Sequence
<220> FEATURE:
<223> OTHER INFORMATION: Synthetic DNA

<400> SEQUENCE: 45
tggatgctga gatcatcatc acca                                         24

<210> SEQ ID NO 46
<211> LENGTH: 23
<212> TYPE: DNA
<213> ORGANISM: Artificial Sequence
<220> FEATURE:
<223> OTHER INFORMATION: Synthetic DNA

<400> SEQUENCE: 46
cgagctcctc gtcgaatttg gaa                                          23

<210> SEQ ID NO 47
<211> LENGTH: 29
<212> TYPE: DNA
<213> ORGANISM: Artificial Sequence
<220> FEATURE:
<223> OTHER INFORMATION: Synthetic DNA

<400> SEQUENCE: 47
caagctgcta agaatgagtt cgaccttga                                    29

<210> SEQ ID NO 48
<211> LENGTH: 26
<212> TYPE: DNA
<213> ORGANISM: Artificial Sequence
<220> FEATURE:
<223> OTHER INFORMATION: Synthetic DNA

<400> SEQUENCE: 48
ttcccacagc ccgctcccaa ggagca                                       26

<210> SEQ ID NO 49
<211> LENGTH: 26
<212> TYPE: DNA
<213> ORGANISM: Artificial Sequence
<220> FEATURE:
<223> OTHER INFORMATION: Synthetic DNA

<400> SEQUENCE: 49
ttccaacagc ccgctcccaa ggagca                                       26

<210> SEQ ID NO 50
<211> LENGTH: 24
<212> TYPE: DNA
<213> ORGANISM: Artificial Sequence
```

```
<220> FEATURE:
<223> OTHER INFORMATION: Synthetic DNA

<400> SEQUENCE: 50
cgatcccgcg aaattaatac gact                                            24

<210> SEQ ID NO 51
<211> LENGTH: 24
<212> TYPE: DNA
<213> ORGANISM: Artificial Sequence
<220> FEATURE:
<223> OTHER INFORMATION: Synthetic DNA

<400> SEQUENCE: 51
tccggatata gttcctcctt tcag                                            24
```

US 8,481,294 B2

MUTANT FORMATE DEHYDROGENASE, GENE ENCODING THE SAME, AND METHOD FOR PRODUCING NADH

CROSS REFERENCE TO RELATED APPLICATIONS

This application is a National Stage of International Application No. PCT/JP2009/063743 filed Aug. 3, 2009 the contents of all of which are incorporated herein by reference in their entirety.

TECHNICAL FIELD

The present invention relates to mutant formate dehydrogenases having substitutional mutations at specific sites in a wild-type formate dehydrogenase, genes encoding the mutant formate dehydrogenases, and a method for producing NADH.

BACKGROUND ART

Formate dehydrogenase (EC.1.2.1.2) reduces $NAD^+$ to reduced nicotinamide adenine dinucleotide (NADH) and oxidizes formic acid to carbon dioxide in the presence of oxidized nicotinamide adenine dinucleotide ($NAD^+$), formic acid, and water. Based on the enzyme reaction, formate dehydrogenase is used for a system for regeneration of NADH from $NAD^+$. Conventionally known examples of formate dehydrogenase include *Candida boidinii* (ATCC32195)-derived formate dehydrogenase as described in JP Patent Publication (Kokai) No. 2003-180383 A, $NAD^+$-dependent-formate dehydrogenase from bacteria of the genus *Bacillus* as disclosed in JP Patent Publication (Kokai) No. 2002-233395 A, and *Mycobacterium vaccae*-derived formate dehydrogenase as disclosed in JP Patent Application No. H10-023896 (1998).

Also, the English translation of BIOCHEMISTRY (Moscow), Vol. 69, No. 11, 2004, pp. 1252-1267 (Biokhimiya, Vol. 69, No. 11, 2004, pp. 1537-1554) discloses formate dehydrogenase from various microorganisms or plants in addition to the above examples. However, as described in this document, the specific activity of formate dehydrogenase is not so significant compared with that of various enzymes. In other words, a method for producing NADH using a formate dehydrogenase reduction reaction to result in NADH can be said to result in poor productivity because of the low specific activity of formate dehydrogenase.

Various research findings regarding formate dehydrogenase have been accumulated to date, and functional alterations by site-directed mutagenesis have been reported (Biomolecular Engineering, 23, (2006) 98-110). However, all conventionally known formate dehydrogenases have low specific activity and low durability. Thus, the use of the formate dehydrogenase must be evaluated as insufficient for NADH production.

DISCLOSURE OF THE INVENTION

Problem to be Solved by the Invention

In view of the above circumstances, the present inventors have applied for a patent concerning formate dehydrogenase exhibiting very high specific activity unpredictable from conventional findings and a method for producing NADH using the formate dehydrogenase (JP Patent Application No. 2008-100448). Hence, an object of the present invention is to provide, as a result of a search for a useful substitutional mutation in the formate dehydrogenase according to this patent application and conventionally known formate dehydrogenases, mutant formate dehydrogenase having better durability than conventionally known mutant formate dehydrogenases, a gene encoding the mutant formate dehydrogenase, and a method for producing NADH using the mutant formate dehydrogenase.

Means for Solving Problem

As a result of intensive studies in order to attain the above object, the present inventors have found that amino acid substitutional mutations at specific sites in the formate dehydrogenase according to the above patent application and in conventionally known formate dehydrogenases significantly improve the durability of formate dehydrogenase, and thus have completed the present invention.

Specifically, the mutant formate dehydrogenase according to the present invention comprises any one amino acid sequence of the following amino acid sequences A) to C) and thus has improved durability:

A) an amino acid sequence that has substitutions of amino acid residues corresponding to the $99^{th}$ valine, the $153^{rd}$ valine, the $155^{th}$ histidine, and the $298^{th}$ asparagine with other amino acids;

B) an amino acid sequence that has substitutions of amino acid residues corresponding to the $73^{rd}$ glycine, the $99^{th}$ valine, the $153^{rd}$ valine, and the $155^{th}$ histidine with other amino acids; and C) an amino acid sequence that has substitutions of amino acid residues corresponding to the $73^{rd}$ glycine, the $99^{th}$ valine, the $153^{rd}$ valine, and the $159^{th}$ glutamine with other amino acids, in the formate dehydrogenase consisting of the amino acid sequence shown in SEQ ID NO: 2.

Also, the mutant formate dehydrogenase according to the present invention preferably comprises an amino acid sequence that has further substitutions of amino acid residues corresponding to 1 to 3 amino acids selected from the group consisting of the $31^{st}$ isoleucine, the $50^{th}$ arginine, the $60^{th}$ glutamic acid, the $64^{th}$ isoleucine, the $73^{rd}$ glycine, the $82^{nd}$ lysine, the 136th isoleucine, the $159^{th}$ glutamine, the $239^{th}$ methionine, the $286^{th}$ aspartic acid, the $287^{th}$ histidine, the $293^{rd}$ glutamic acid, and the $343^{rd}$ asparagine with other amino acids, with respect to the above amino acid sequence A).

Furthermore, the mutant formate dehydrogenase according to the present invention preferably comprises an amino acid sequence that has further substitutions of amino acid residues corresponding to 1 to 3 amino acids selected from the group consisting of the $31^{st}$ isoleucine, the $50^{th}$ arginine, the $60^{th}$ glutamic acid, the $64^{th}$ isoleucine, the $82^{nd}$ lysine, the $136^{th}$ isoleucine, the $159^{th}$ glutamine, the $239^{th}$ methionine, the $286^{th}$ aspartic acid, the $287^{th}$ histidine, the $293^{rd}$ glutamic acid, the $298^{th}$ asparagine, and the $343^{rd}$ asparagine with other amino acids, with respect to the above amino acid sequence B).

Furthermore, the mutant formate dehydrogenase according to the present invention preferably comprises an amino acid sequence that has further substitutions of amino acid residues corresponding to 1 to 3 amino acids selected from the group consisting of the $31^{st}$ isoleucine, the $50^{th}$ arginine, the $60^{th}$ glutamic acid, the $64^{th}$ isoleucine, the $82^{nd}$ lysine, the $136^{th}$ isoleucine, the $155^{th}$ histidine, the $239^{th}$ methionine, the $286^{th}$ aspartic acid, the $287^{th}$ histidine, the $293^{rd}$ glutamic acid, the 298th asparagine, and the 343rd asparagine with other amino acids, with respect to the above amino acid sequence C).

Here, amino acids after substitutional mutation are not particularly limited. For example, an amino acid after substitution of the above amino acid corresponding to the 31st isoleucine can be leucine, an amino acid after substitution of the above amino acid corresponding to the 50th arginine can be glycine, an amino acid after substitution of the above amino acid corresponding to the 60th glutamic acid can be valine, an amino acid after substitution of the above amino acid corresponding to the 64th isoleucine can be valine, an amino acid after substitution of the above amino acid corresponding to the 73rd glycine can be alanine, an amino acid after substitution of the above amino acid corresponding to the 82nd lysine can be arginine, an amino acid after substitution of the above amino acid corresponding to the 99th valine can be isoleucine, an amino acid after substitution of the above amino acid corresponding to the 136th isoleucine can be valine, an amino acid after substitution of the above amino acid corresponding to the 153rd valine can be isoleucine, an amino acid after substitution of the above amino acid corresponding to the 155th histidine can be glutamine or lysine, an amino acid after substitution of the above amino acid corresponding to the 159th glutamine can be leucine or asparagine, an amino acid after substitution of the above amino acid corresponding to the 239th methionine can be leucine, amino acid after substitution of the above amino acid corresponding to the 286th aspartic acid can be phenylalanine, an amino acid after substitution of the above amino acid corresponding to the 287th histidine can be glutamine or proline, an amino acid after substitution of the above amino acid corresponding to the 293rd glutamic acid can be aspartic acid, an amino acid after substitution of the above amino acid corresponding to the 298th asparagine can be tyrosine, and an amino acid after substitution of the above amino acid corresponding to the 343rd asparagine can be arginine.

Also, the method for producing NADH according to the present invention comprises causing the above-mentioned mutant formate dehydrogenase according to the present invention to act on a reaction system containing formic acid and $NAD^+$.

Effects of the Invention

The mutant formate dehydrogenase according to the present invention has a feature such that the durability is significantly improved compared with formate dehydrogenase before mutation thereof due to a novel substitutional mutation(s). With the use of the mutant formate dehydrogenase according to the present invention, NADH known as a very expensive substance can be produced with good productivity. NADH production using the mutant formate dehydrogenase according to the present invention enables industrial production of NADH.

BRIEF DESCRIPTION OF THE DRAWINGS

FIG. 1-1 to 1-2 are characteristic diagrams showing the results of multiple alignment analysis for *Gibberella zeae*-derived FDH (SEQ ID NO: 2), *Pseudomonas* sp. 101-derived FDH (SEQ ID NO: 3), *Mycobacterium vaccae* N10.-derived FDH (SEQ ID NO: 4), *Candida boidini*-derived FDH (SEQ ID NO: 6), *Candida methylica*-derived FDH (SEQ ID NO: 8), *Saccharomyces cerevisiae*-derived FDH (SEQ ID NO: 10), and *Paracoccus* sp.12-A-derived FDH (SEQ ID NO: 12), as well as a novel mutation(s) according to the present invention and a known mutation(s).

FIG. 2 is a schematic diagram showing the steps for constructing GzFDH/pET23b(+).

BEST MODE FOR CARRYING OUT THE INVENTION

Figure 2:
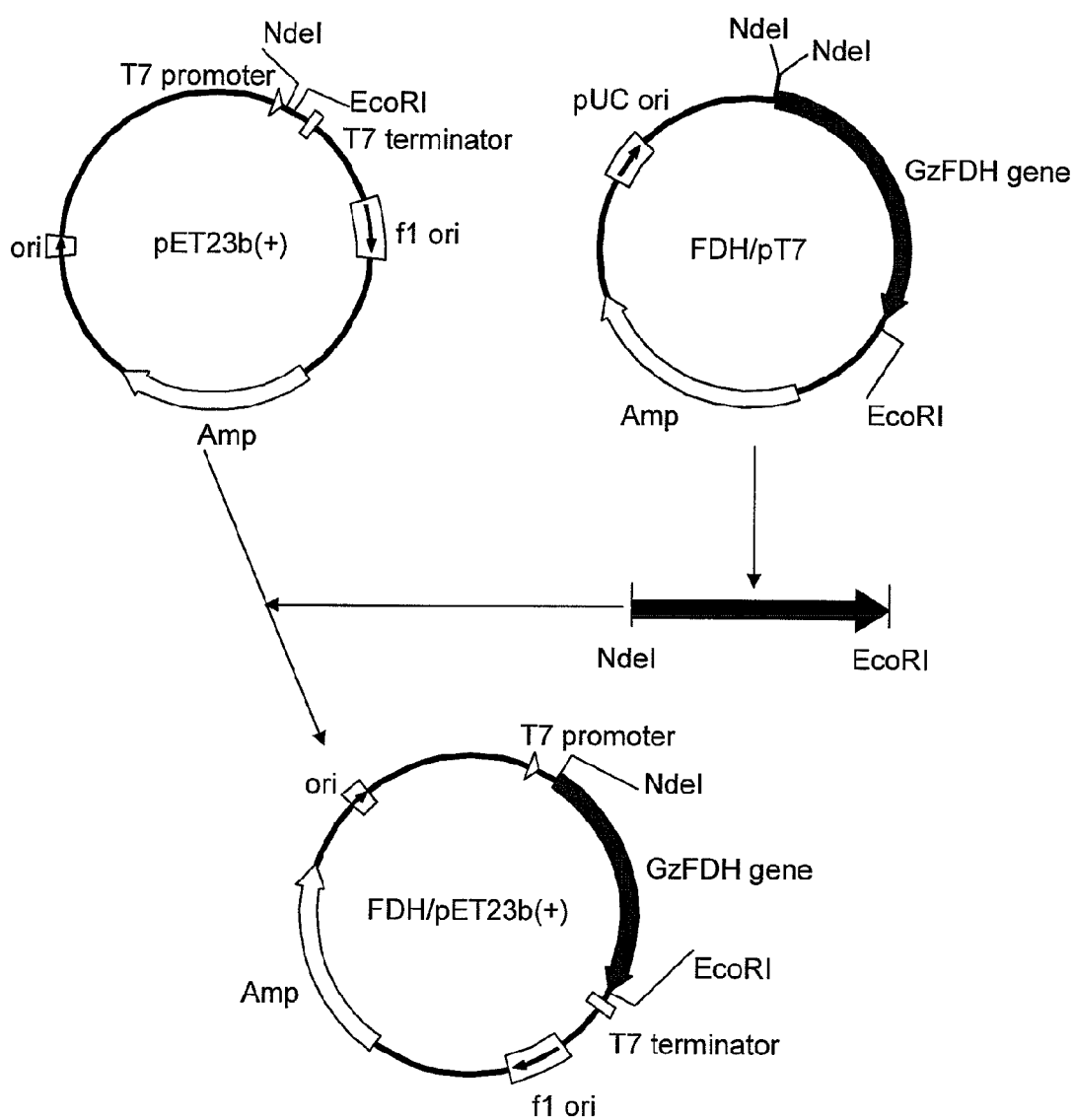

The present invention will be described in detail as follows, referring to the drawings.

Formate Dehydrogenase

The mutant formate dehydrogenase according to the present invention has an amino acid sequence that has substitutions of specific amino acid residues in a formate dehydrogenase. Here, formate dehydrogenase is not particularly limited, as long as it has amino acid residues to be substituted as specifically described later and formate dehydrogenase activity. Specifically, formate dehydrogenase is an enzyme, which is classified into EC1.2.1.2 under the enzyme classification, oxidizes formic acid ions to carbon dioxide, and has activity of catalyzing a reaction for reducing $NAD^+$ ions to NADH.

The formate dehydrogenase may be a plant-derived enzyme, an animal-derived enzyme, or a microorganism-derived enzyme. Examples of the microorganism-derived formate dehydrogenase include various formate dehydrogenases as disclosed in the overview concerning formate dehydrogenase (Biomolecular Engineering 23 (2006) 98-110). More specifically, the present invention can be applied to *Staphylococcus aureus*-derived formate dehydrogenase (Baba, T. et al., Lancet 359, 1819-1827, 2002), *Mycobacterium avium* subsp. *paratuberculosis* str.k10 (Li et al., Proc. Natl. Acad. Sci. U.S.A. 102, 12344-12349, 2005), *Bordetella*-derived formate dehydrogenase (Parkhill et al., Nat. Genet. 35, 32-40., 2003), *Legionella*-derived formate dehydrogenase (Chien et al., Science 305, 1966 v 1968, 2004, and Cazalet et al., Nat. Genet. 36, 1165-1173, 2004), *Francisella tularensis* subsp. *tularensis* SCHU S4-derived formate dehydrogenase (Larsson et al., Nat. Genet. 37, 153-159, 2005), *Histoplasma capsulatum*-derived formate dehydrogenase (Hwang et al., Mol. Biol. Cell 14, 2314-2326, 2003), *Cryptococcus neoformans* var. *neoformans* JEC21 (Loftus et al., Science 307, 1321-1324, 2005), and the like revealed by recent genomic analysis.

The present invention can also be applied to *Pseudomonas* sp. 101-derived formate dehydrogenase, *Mycobacterium vaccae* N10.-derived formate dehydrogenase, *Candida boidini*-derived formate dehydrogenase, *Candida methylica*-derived formate dehydrogenase, *Saccharomyces cerevisiae*-derived formate dehydrogenase, and *Paracoccus* sp. 12-A-derived formate dehydrogenase disclosed in the above overview.

In particular, the present invention is preferably applied to *Gibberella zeae*-derived formate dehydrogenase that has been previously applied for a patent (JP Patent Application No. 2008-100448). *Gibberella zeae*-derived formate dehydrogenase exhibits specific activity significantly better than that of the above-mentioned conventionally known formate dehydrogenases. The nucleotide sequence of a gene encoding *Gibberella zeae*-derived formate dehydrogenase is shown in SEQ ID NO: 1. The amino acid sequence of *Gibberella zeae*-derived formate dehydrogenase is shown in SEQ ID NO: 2. To obtain formate dehydrogenase, conventionally known various microbial strains that have been preserved as *Fusarium* (scientific name: *Gibberella zeae*) can be used. For example, *Fusarium* strains preserved at the American Type Culture Collection (ATCC) under ATCC No. 10910, No. 20271, No. 20272, No. 20274, No. 24689, No. 28106, or No. 48063 can be used. Also, *Fusarium* strains are preserved at the ATCC under registration name of *Fusarium graminearum*. If *Gibberella zeae* is registered under another name, this can also be used herein. In addition, *Gibberella zeae* to be used herein indicates *Fusarium graminearum* at the perfect stage (teleomorph). Also, *Fusarium* preserved at the NITE Biological Resource Center (NBRC) under NBRC No. 4474, No. 5269, No. 6608, No. 7160, No. 7520, No. 7772, No. 8850, or No. 9462 can also be used herein. Moreover, formate dehydrogenase may also be obtained without using microbial strains preserved at institutions such as ATCC and NBRC, but instead using *Fusarium* independently isolated from nature.

The amino acid sequence of *Pseudomonas* sp. 101-derived formate dehydrogenase is shown in SEQ ID NO: 3. The amino acid sequence of *Mycobacterium vaccae* N10.-derived formate dehydrogenase is shown in SEQ ID NO: 4. The nucleotide sequence of a gene encoding *Candida boidini*-derived formate dehydrogenase is shown in SEQ ID NO: 5. The amino acid sequence of *Candida boidini*-derived formate dehydrogenase is shown in SEQ ID NO: 6. The nucleotide sequence of a gene encoding *Candida methylica*-derived formate dehydrogenase is shown in SEQ ID NO: 7. The amino acid sequence of *Candida methylica*-derived formate dehydrogenase is shown in SEQ ID NO: 8. The nucleotide sequence of a gene encoding *Saccharomyces cerevisiae*-derived formate dehydrogenase is shown in SEQ ID NO: 9. The amino acid sequence of *Saccharomyces cerevisiae*-derived formate dehydrogenase is shown in SEQ ID NO: 10. The nucleotide sequence of a gene encoding *Paracoccus* sp. 12-A-derived formate dehydrogenase is shown in SEQ ID NO: 11. The amino acid sequence of *Paracoccus* sp. 12-A-derived formate dehydrogenase is shown in SEQ ID NO: 12.

Formate dehydrogenase that can be used in the present invention is not limited to the one consisting of the amino acid sequence shown in SEQ ID NO: 2, 3, 4, 6, 8, 10, or 12. An example thereof to be used herein may be formate dehydrogenase that comprises an amino acid sequence that has a deletion, a substitution, an addition, or an insertion of 1 or a plurality of amino acids excluding amino acid residues to be substituted as described in detail later, with respect to the amino acid sequence shown in SEQ ID NO: 2, 3, 4, 6, 8, 10, or 12, and has catalytic activity in a reaction wherein formic acid and $NAD^+$ are substrates and carbon dioxide and NADH are products. Here, the term "a plurality of amino acids" refers to, for example, 1 to 30, preferably 1 to 20, more preferably, 1 to 10, further more preferably 1 to 5, and particularly preferably 1 to 3 amino acids. In addition, deletion, substitution, or addition of amino acids can be performed by altering the nucleotide sequence encoding the above gene by a technique known in the art. Mutation can be introduced into a nucleotide sequence by known techniques such as Kunkel method or Gapped duplex method or methods according thereto. For example, mutation is introduced using a mutagenesis kit using site-directed mutagenesis (e.g., Mutant-K and Mutant-G (both are commercial names, TAKARA)) or a LA PCR in vitro Mutagenesis series kit (trade name, TAKARA).

Also, formate dehydrogenase that can be used in the present invention comprises an amino acid sequence that has 85% or more, preferably 90% or more, more preferably 95% or more, and most preferably 98% or more homology, for example, with the amino acid sequence shown in SEQ ID NO: 2, 3, 4, 6, 8, 10, or 12, and has catalytic activity in a reaction wherein formic acid and $NAD^+$ are substrates and carbon dioxide and NADH are products. Here, the value of homology refers to a value that is found using a database with default setting, in which a computer program with blast algorithm mounted therein and gene sequence information are stored.

Furthermore, a protein that can be used as formate dehydrogenase in the present invention is a protein that is encoded by polynucleotide hybridizing under stringent conditions to polynucleotide complementary to a portion of or the entire nucleotide sequence shown in SEQ ID NO: 1, 5, 7, 9, or 11 and has catalytic activity in a reaction in which formic acid and $NAD^+$ are substrates and carbon dioxide and NADH are products. Here, the expression, "hybridizing under stringent conditions" means that binding is maintained under washing conditions of 60° C. and 2×SSC. Hybridization can be performed by a conventionally known method such as the method described in J. Sambrook et al. Molecular Cloning, A Laboratory Manual, 2nd Ed., Cold Spring Harbor Laboratory (1989).

Substitutional Mutation

The mutant formate dehydrogenase according to the present invention is prepared by substituting a plurality of predetermined amino acid residues in the above-mentioned formate dehydrogenase, having significantly improved durability compared with that of formate dehydrogenase before amino acid substitution. Here, amino acid residues to be substituted can be specified using numerical values counted from the N-terminus on the basis of *Gibberella zeae*-derived formate dehydrogenase consisting of the amino acid sequence shown in SEQ ID NO: 2. However, amino acid residues to be substituted, which are specified with specific numerical values found on the basis of the amino acid sequence shown in SEQ ID NO: 2 are represented by different numerical values depending on the types of formate dehydrogenase. Therefore, in the case of expression, "Xth (or Xrd) amino acid residue (at position X) in the amino acid sequence shown in SEQ ID NO: 2," an amino acid residue (corresponding to the Xth or Xrd amino acid residue) in formate dehydrogenase that has an amino acid sequence differing from the amino acid sequence shown in SEQ ID NO: 2 is represented by a numerical value differing from "X."

An amino acid residue (in an amino acid sequence differing from the amino acid sequence shown in SEQ ID NO: 2) corresponding to such a predetermined amino acid residue in the amino acid sequence shown in SEQ ID NO: 2 can be specified by multiple alignment analysis for a plurality of amino acid sequences including the amino acid sequence shown in SEQ ID NO: 2. Multiple alignment analysis can be easily performed by persons killed in the art using a CLUSTAL W (1.83) multiple sequence alignment program (that can be used with DDBJ of the National Institute of Genetics clustalw.ddbj.nig.ac.jp/top-j.html)), for example. But the example thereof is not limited thereto. In addition, with the use of a pair-wise alignment analysis method, another different amino acid sequence is aligned with the amino acid sequence shown in SEQ ID NO: 2, amino acid residues corresponding to predetermined amino acid residues in the amino acid sequence shown in SEQ ID NO: 2 can also be specified in the different amino acid sequence.

FIG. 1 shows the results of multiple alignment analysis for *Gibberella zeae*-derived formate dehydrogenase (SEQ ID NO: 2), *Pseudomonas* sp. 101-derived formate dehydrogenase (SEQ ID NO: 3), *Mycobacterium vaccae* N10.-derived formate dehydrogenase (SEQ ID NO: 4), *Candida boidinii*-derived formate dehydrogenase (SEQ ID NO: 6), *Candida methylica*-derived formate dehydrogenase (SEQ ID NO: 8), *Saccharomyces cerevisiae*-derived formate dehydrogenase (SEQ ID NO: 10), and *Paracoccus* sp. 12-A-derived formate dehydrogenase (SEQ ID NO: 12). In addition, formate dehydrogenases other than these specific formate dehydrogenases can also be similarly subjected to multiple alignment analysis, so that they can be compared with *Gibberella zeae*-derived formate dehydrogenase (SEQ ID NO: 2).

In the following explanation, amino acids to be substituted are denoted on the basis of the amino acid sequence shown in SEQ ID NO: 2; that is, *Gibberella zeae*-derived formate dehydrogenase. However, as described above, it should be noted that numerical values representing the positions of amino acids differ for different formate dehydrogenases. Examples of the mutant formate dehydrogenase according to the present invention include quadruple mutant formate dehydrogenase, which has substitutional mutations of amino acid residues at 4 positions described later and mutant formate dehydrogenase, which has other substitutional mutations at 1 to 3 positions of the quadruple mutant formate dehydrogenase.

Quadruple Mutant Formate Dehydrogenase

The quadruple mutant formate dehydrogenase according to the present invention has the amino acid sequence shown in any one of the following A) to C):

A) an amino acid sequence having substitutions of the $99^{th}$ valine, the $153^{rd}$ valine, the $155^{th}$ histidine, and the $298^{th}$ asparagine with other amino acids;
B) an amino acid sequence having substitutions of the $73^{rd}$ glycine, the $99^{th}$ valine, the $153^{rd}$ valine, and the $155^{th}$ histidine with other amino acids; and
C) an amino acid sequence having substitutions of the $73^{rd}$ glycine, the $99^{th}$ valine, the $153^{rd}$ valine, and the $159^{th}$ glutamine with other amino acids.

In the above amino acid sequences A) to C), examples of "other amino acids" are not particularly limited and may be any amino acids, as long as the durability of formate dehydrogenase after mutation is significantly improved compared with that of formate dehydrogenase before mutation. Durability can be evaluated with remaining activity found after an object is left to stand at 37° C. for 500 hours. In addition, durability may also be evaluated with an acceleration test, by which an object is left to stand at 37° C. for 500 hours (e.g., under conditions wherein an object is left to stand at 52° C. to 58° C. for 30 minutes to 50 minutes). Also, the expression "durability is improved" means that remaining activity after mutagenesis is statistically significantly higher than that of wild-type formate dehydrogenase before mutagenesis. Here, the enzyme activity of mutant formate dehydrogenase and the same of formate dehydrogenase before substitutional mutation can be determined by appropriately using conventionally known techniques. For example, through direct or indirect measurement of the amount of NADH generated according to the following formula (reaction formula) or the amounts of components consumed according to the following reaction formula, the enzyme activity of formate dehydrogenase contributing to the following formula can be measured.

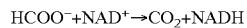

In particular, in the above amino acid sequences A) to C), a substitutional mutation of the $73^{rd}$ glycine to alanine, a substitutional mutation of the $99^{th}$ valine to isoleucine, a substitutional mutation of the $153^{rd}$ valine to isoleucine, a substitutional mutation of the $155^{th}$ histidine to glutamine or lysine, a substitutional mutation of the $159^{th}$ glutamine to leucine, and a substitutional mutation of the $298^{th}$ asparagine to tyrosine are preferred.

In addition, as described above, amino acids specifically preferable as amino acids after substitution are exemplified, but the examples of amino acids after substitution are not limited to the above examples. As also described in reference (1) ("McKee Biochemistry (Biochemistry: the molecular basis of life)" $3^{rd}$ ed., Chapter 5 Amino Acid.Peptide.Protein 5.1 Amino acid, Edition: Atsushi Ichikawa, supervised translation: Shinichi Fukuoka, publisher: Ryosuke Sone, publishing office: Kagaku-Dojin Publishing Company, Inc., ISBN4-7598-0944-9), it is well known that amino acids are classified based on side chains having similar properties (e.g., chemical properties and physical size). It is also well known that molecular evolutional substitution takes place with high frequency between amino acid residues that are classified in a given group, while the protein activity is maintained. Based on this concept, score matrix (BLOSUM) for substitutional mutation of amino acid residues has been proposed as in FIG. 2 of reference (2): Henikoff S., Henikoff J. G., Amino-acid substitution matrices from protein blocks, Proc. Natl. Acad. Sci. U.S.A., 89, 10915-10919 (1992) and is broadly used. Reference (2) is based on the finding such that substitution between amino acids having similar chemical properties of side chains cause less structural or functional changes on the entire protein. According to references (1) and (2) above, amino acid side chain groups to be taken into consideration for multiple alignment may be determined based on indices such as chemical properties, physical size, and the like. These groups are shown by score matrix (BLOSUM) disclosed in reference (2) as groups of amino acids having the score of 0 or more and amino acids preferably having the score of 1 or more.

Based on the above findings, amino acids having properties analogous to each other can be classified into the following 8 groups. Therefore, amino acids after substitution are preferably amino acids that are classified in groups including the above exemplified amino acids. For example, the 99$^{th}$ valine in *Gibberella zeae*-derived formate dehydrogenase is preferably substituted with isoleucin, or may be substituted with leucine, methionine, or valine that is classified in the following 1) aliphatic hydrophobic amino acid group in which isoleucine is classified. Similarly, the 155$^{th}$ histidine in *Gibberella zeae*-derived formate dehydrogenase is preferably substituted with glutamine or lysine, or may be substituted with glutamic acid or arginine that is classified in the following 6) group of methylene group=polar group in which glutamine and lysine are classified. Also, the 159$^{th}$ glutamine in *Gibberella zeae*-derived formate dehydrogenase is preferably substituted with leucine, or may be substituted with isoleucine, methionine, or valine that is classified in the following 1) aliphatic hydrophobic amino acid group in which leucine is classified. Furthermore, the 298$^{th}$ asparagine in *Gibberella zeae*-derived formate dehydrogenase is preferably substituted with tyrosine, or may be substituted with phenylalanine or tryptophan that is classified in the following 7) aromatic group in which tyrosine is classified or with histidine that is classified in the following 8) ring & polar group.

1) Aliphatic Hydrophobic Amino Acid Group (ILMV Group)

This group is a group of neutral non-polar amino acids (described in reference (1) above) having aliphatic hydrophobic side chains, which is composed of V (Val, valine), L (Leu, leucine), I (Ile, isoleucine), and M (Met, methionine). Of those classified as neutral non-polar amino acids as in reference (1), FGACWP is not included in the "aliphatic hydrophobic amino acid group" because of the following reasons. G (Gly, glycine) or A (Ala, alanine) is of the same size as or smaller than a methyl group and thus has a weak non-polar effect. C (Cys, cysteine) may play an important role in S—S linkage, and, has a feature such that it forms a hydrogen bond with an oxygen atom or a nitrogen atom. F (Phe, phenylalanine) and W (Trp, tryptophan) have side chains with particularly high molecular weights, and thus have a strong aromatic effect. P (Pro, proline) has a strong imino acid effect, so as to fix the angle of the main chain of the polypeptide.

2) Group Having Hydroxymethylene Group (ST Group)

This group is a group of neutral polar amino acids having hydroxymethylene groups in the side chains, which is composed of S (Ser, serine) and T (Thr, threonine). Hydroxyl groups existing in S and T side chains are sugar-binding sites, so that the sites are often important for polypeptides (proteins) to have specific activity.

3) Acidic Amino Acid Group (DE Group)

This group is a group of amino acids having acidic carboxyl groups in the side chains, which is composed of D (Asp, aspartic acid) and E (Glu, glutamic acid).

4) Basic Amino Acid Group (KR Group)

This group is a group of basic amino acids, which is composed of K (Lys, lysine) and R (Arg, arginine). These K and R are positively charged within a wide pH range and thus have basic properties. Meanwhile, H (His, histidine) that is classified as basic amino acid is almost never ionized at pH 7 and thus is not classified in this group.

5) Methylene Group=Polar Group (DHN Group)

This group is characterized in that methylene groups bind as side chains to all carbon elements at position a beyond which a polar group is present. The group is also characterized in that the physical sizes of methylene groups as non-polar groups closely resemble to each other, which is composed of N (Asn, asparagine, and the polar group is an amide group), D (Asp, aspartic acid, and the polar group is a carboxyl group), and H (His, histidine, and the polar group is an imidazole group).

6) Dimethylene Group=Polar Group (EKQR Group)

This group is characterized in that linear hydrocarbons each having carbon chain length longer than a dimethylene group bind as side chains to all carbon elements at position a beyond which a polar group is present, and the physical sizes of dimethylene groups as non-polar groups closely resemble from each other. The group is composed of E (Glu, glutamic acid, and the polar group is a carboxyl group), K (Lys, lysine, and the polar group is an amino group), Q (Gln, glutamine, and the polar group is an amide group), and R (Arg, arginine, and the polar groups are an imino group and an amino group).

7) Aromatic Group (FYW Group)

This group is a group of aromatic amino acids having benzene nuclei in side chains and is characterized by chemical properties peculiar to the aromatic group. The group is composed of F (Phe, phenylalanine), Y (Tyr, tyrosine), and W (Trp, tryptophan).

8) Ring & Polar Group (HY Group)

This group is a group of amino acids having ring structures in side chains, in addition to polarity, which is composed of H (H, histidine, and both ring structure and polar group are imidazole groups), Y (Tyr, tyrosine, and the ring structure is a benzene nucleus and the polar group is a hydroxyl group).

Quintuple, Hexatic, and Septuple Mutant Formate Dehydrogenases

Quintuple, hexatic, and septuple mutant formate dehydrogenases can be obtained by further introducing 1 to 3 substitutional mutations to the above-mentioned quadruple mutant formate dehydrogenase. Examples of further 1 to 3 substitutional mutations include amino acids at positions other than mutation positions in the above amino acid sequences A) to C), such as the 31$^{st}$ isoleucine, the 50$^{th}$ arginine, the 60$^{th}$ glutamic acid, the 64$^{th}$ isoleucine, the 73$^{rd}$ glycine, the 82$^{nd}$ lysine, the 136$^{th}$ isoleucine, the 155$^{th}$ histidine, the 159$^{th}$ glutamine, the 239$^{th}$ methionine, the 286$^{th}$ aspartic acid, the 287$^{th}$ histidine, the 293$^{rd}$ glutamic acid, the 298$^{th}$ asparagine, and the 343$^{rd}$ asparagine in the amino acid sequence shown in SEQ ID NO: 2.

Amino acid residues listed herein are not particularly limited, as long as the durability of formate dehydrogenase after mutation is significantly improved compared with the same of wild-type formate dehydrogenase, and may be substituted with any amino acid. Particularly, a substitutional mutation of the 31$^{st}$ isoleucine to leucine, a substitutional mutation of the 50$^{th}$ arginine to glycine, a substitutional mutation of the 60$^{th}$ glutamic acid to valine, a substitutional mutation of the 64$^{th}$ isoleucine to valine, a substitutional mutation of the 73$^{rd}$ glycine to alanine, a substitutional mutation of the 82$^{nd}$ lysine to arginine, a substitutional mutation of the 136$^{th}$ isoleucine to valine, a substitutional mutation of the 155$^{th}$ histidine to glutamine or lysine, a substitutional mutation of the 159$^{th}$ glutamine to leucine or asparagine, a substitutional mutation of the 239$^{th}$ methionine to leucine, a substitutional mutation of the 286$^{th}$ aspartic acid to phenylalanine, a substitutional mutation of the 287$^{th}$ histidine to glutamine or proline, a substitutional mutation of the 293$^{rd}$ glutamic acid to aspartic acid, a substitutional mutation of the 298$^{th}$ asparagine to tyrosine, and a substitutional mutation of the 343$^{rd}$ asparagine to arginine are preferred. In addition, preferable amino acid types of the amino acid residues listed herein after substitutional mutation are disclosed. In a manner similar to the above, amino acid types after substitutional mutation can be appropriately selected based on the above 8 groups in which amino acids having analogous properties are classified.

Also, in particular, an example of the quintuple mutant formate dehydrogenase is a mutant formate dehydrogenase having substitutional mutation (abbreviated as G73A using single character codes for amino acids, and the same applies to the following) of the 73$^{rd}$ glycine to alanine, V99I, V153I, H155Q, and N298Y. The quintuple mutant formate dehydrogenase having these G73A, V99I, V153I, H155Q, and N298Y can exhibit good durability as defined above while maintaining specific activity equivalent to that of a wild-type formate dehydrogenase.

Furthermore, an example of the quintuple mutant formate dehydrogenase is a mutant formate dehydrogenase having G73A, V99I, V153I, H155Q, and H287Q. The quintuple mutant formate dehydrogenase having these G73A, V99I, V153I, H155Q, and H287Q can also exhibit good durability.

Furthermore, an example of the quintuple mutant formate dehydrogenase is a mutant formate dehydrogenase having G73A, V99I, V153I, H155K, and N298Y. The quintuple mutant formate dehydrogenase having these G73A, V99I, V153I, H155K, and N298Y can also exhibit good durability. In addition, as described in Examples below, the quintuple mutant formate dehydrogenase having G73A, V99I, V153I, H155K, and N298Y was compared with the quintuple mutant formate dehydrogenase having G73A, V99I, V153I, H155Q, and N298Y in terms of durability. As a result, the quintuple mutant formate dehydrogenase having G73A, V99I, V153I, H155K, and N298Y exhibited better durability. Therefore, it can be understood that lysine is more preferable than glutamine as amino acid after substitutional mutation of the 155$^{th}$ histidine.

Furthermore, examples of the quintuple mutant formate dehydrogenase include a mutant formate dehydrogenase having G73A, V99I, V153I, Q159L, and N298Y, and a mutant formate dehydrogenase having V99I, V153I, H155Q, H287Q, and N298Y. These quintuple mutant formate dehydrogenases can also exhibit durability better than that of the wild-type formate dehydrogenase, in a manner equivalent to that of the quintuple mutant formate dehydrogenase having G73A, V99I, V153I, H155Q, and N298Y.

Furthermore, examples of the quintuple mutant formate dehydrogenase include a mutant formate dehydrogenase having E60V, G73A, V99I, V153I, and H155Q, and a mutant formate dehydrogenase having E60V, V99I, V153I, H155Q, and N298Y. These quintuple mutant formate dehydrogenases can also exhibit higher degrees of durability than wild-type formate dehydrogenase.

Meanwhile, a preferable example of the hexatic mutant formate dehydrogenase is prepared by further introducing one substitutional mutation selected from M239L, K82R, H287Q, E60V, I31L, I136V, and E293D into the quintuple mutant formate dehydrogenase having G73A, V99I, V153I, H155Q, and N298Y. The hexatic mutant formate dehydrogenase can exhibit a higher degree of durability than the quintuple mutant formate dehydrogenase having G73A, V99I, V153I, H155Q, and N298Y. Also, a hexatic mutant formate dehydrogenase having G73A, V99I, V153I, H155Q, M239L, and N298Y, a hexatic mutant formate dehydrogenase having E60V, G73A, V99I, V153I, H155Q, and N298Y, and a hexatic mutant formate dehydrogenase having G73A, V99I, V153I, H155K, M239L, and N298Y can exhibit not only a high degree of durability as described above, but also better specific activity than the wild-type formate dehydrogenase.

Also, an example of the hexatic mutant formate dehydrogenase is the one prepared by introducing M239L into the above quintuple mutant formate dehydrogenase having G73A, V99I, V153I, Q159L, and N298Y. Through introduction of M239L, specific activity can be improved while maintaining durability equivalent to that of the above quintuple mutant formate dehydrogenase having G73A, V99I, V153I, Q159L, and N298Y.

Furthermore, an example of the hexatic mutant formate dehydrogenase is the one prepared by introducing H287P into the quintuple mutant formate dehydrogenase having G73A, V99I, V153I, H155Q, and N298Y. However, when compared with the hexatic mutant formate dehydrogenase prepared by introducing H287Q into the quintuple mutant formate dehydrogenase having G73A, V99I, V153I, H155Q, and N298Y, as described above, decreased specific activity was observed. Therefore, it can be understood that as an amino acid after substitutional mutation of the 287$^{th}$ histidine, glutamine is more preferable than proline.

Furthermore, an example of the hexatic mutant formate dehydrogenase is the one prepared by introducing R50G or N343R into the quintuple mutant formate dehydrogenase having G73A, V99I, V153I, H155Q, and N298Y. These hexatic mutant formate dehydrogenases can also exhibit durability equivalent to that of the quintuple mutant formate dehydrogenase having G73A, V99I, V153I, H155Q, and N298Y.

Furthermore, an example of the hexatic mutant formate dehydrogenase is the one prepared by introducing K82R or Q159L into the quintuple mutant formate dehydrogenase having G73A, V99I, V153I, H155K, and N298Y. The hexatic mutant formate dehydrogenase can exhibit durability better than that of the quintuple mutant formate dehydrogenase having G73A, V99I, V153I, H155K, and N298Y.

Furthermore, examples of the hexatic mutant formate dehydrogenase include a mutant formate dehydrogenase having I64V, G73A, V99I, V153I, H155Q, and N298Y and a mutant formate dehydrogenase having G73A, V99I, V153I, H155Q, Q159N, and N298Y. These quintuple mutant formate dehydrogenases can also exhibit durability better than that of wild-type formate dehydrogenase.

Meanwhile, an example of the septuple mutant formate dehydrogenase is the one prepared by introducing K82R into the above hexatic mutant formate dehydrogenase having G73A, V99I, V153I, H155Q, M239L, and N298Y. The septuple mutant formate dehydrogenase can exhibit both durability and specific activity better than those of the above hexatic mutant formate dehydrogenase having G73A, V99I, V153I, H155Q, M239L, and N298Y.

Also, examples of the septuple mutant formate dehydrogenase include a septuple mutant formate dehydrogenase having G73A, K82R, V99I, V153I, H155Q, H287Q, and N298Y, a septuple mutant formate dehydrogenase having G73A, V99I, V153I, H155Q, Q159L, M239L, and N298Y, and a septuple mutant formate dehydrogenase having G73A, V99I, V153I, H155Q, Q159L, H287Q, and N298Y. These septuple mutant formate dehydrogenases can also exhibit durability better than that of wild-type formate dehydrogenase.

Furthermore, examples of the septuple mutant formate dehydrogenase include a septuple mutant formate dehydrogenase having G73A, V99I, V153I, H155Q, D286F, H287P, and N298Y and a septuple mutant formate dehydrogenase having G73A, V99I, V153I, H155Q, D286F, H287P, and N298Y. These septuple mutant formate dehydrogenases can also exhibit durability better than that of wild-type formate dehydrogenase.

Production of *Fusarium*-derived Formate Dehydrogenase

Among the above examples of the mutant formate dehydrogenase according to the present invention, a mutant formate dehydrogenase derived from *Fusarium* (*Gibberella zeae*)-derived formate dehydrogenase exhibits very high specific activity even before substitutional mutation. Therefore, a mutant formate dehydrogenase derived from *Fusarium*-derived formate dehydrogenase is preferable since the durability and/or specific activity thereof are significantly higher than those of mutant formate dehydrogenases derived from other organisms-derived formate dehydrogenases.

Here, the *Fusarium*-derived formate dehydrogenase cannot be obtained by conventionally known methods for protein production. Therefore, obtainment of the *Fusarium*-derived mutant formate dehydrogenase by conventionally known methods for protein production is also difficult. The *Fusarium*-derived mutant formate dehydrogenase can be produced according to techniques described below. Specifically, a method for producing the *Fusarium*-derived formate dehydrogenase comprises preparing a host by introducing a vector in which a *Fusarium*-derived formate dehydrogenase gene is arranged under control of an inducible promoter, culturing the host, inducing the expression of the formate dehydrogenase gene after the logarithmic growth phase, culturing the host at a temperature that is lower than the optimum temperature for the growth of the host and allows the survival of the host, and thus causing the expression of the formate dehydrogenase within the host.

As an inducible promoter to be used in the method for producing the *Fusarium*-derived formate dehydrogenase, any conventionally known promoter can be used without particular limitation. For example, when *Escherichia coli* is used as the above host, an inducible promoter exhibiting transcriptional activity in the presence of isopropyl-β-thiogalactopyranoside (IPTG) can be used. Examples of such a promoter include Trp promoter, Lac promoter, Trc promoter, and Tac promoter. Moreover, another promoter exhibiting transcriptional activity in the presence of an inducing substance other than IPTG and another promoter exhibiting transcriptional activity according to culture conditions of medium components, temperature, and the like can also be used as inducible promoters.

Also, any vector can be used without particular limitation in the method for producing the *Fusarium*-derived formate dehydrogenase, as long as it is replicable within the above host. For example, when *Escherichia coli* is used as the above host, a vector may be either a plasmid vector or a phage vector. Specific examples of a vector include pCDF series, pRSF series, and pET series.

Furthermore, a host to be used herein is not particularly limited, as long as it enables transcription from a promoter incorporated into an expression vector. For example, when an expression vector is a pET (T7 promoter)-based vector, *Escherichia coli* BL21 (DE3) can be used. As techniques for introducing the above vector into a host, various techniques generally known as transformation methods can be applied. As specific techniques, for example, a calcium phosphate method, electroporation, lipofection, and the like can be applied.

Particularly in the method for producing the *Fusarium*-derived formate dehydrogenase, a host into which a vector has been introduced is cultured, and then the expression of the formate dehydrogenase gene is induced after the logarithmic growth phase. Culture conditions for a host before induction of the expression of the formate dehydrogenase gene are not particularly limited. For example, the culture conditions may be appropriately determined in view of the optimum temperature and the optimum pH for the growth of the relevant host. However, the growth of the host is observed while continuing culture. At a time point after the logarithmic growth phase, the culture conditions are changed so as to satisfy the following requirements: Requirement 1 is to induce the expression of the formate dehydrogenase gene and requirement 2 is to culture the host at a temperature that is lower than the optimum temperature for the growth of the host, but allows the survival of the host.

Here, the expression "after the logarithmic growth phase" refers to the time point at which the tangential slope begins to decrease from a portion that is an approximately straight line with a predetermined slope on a growth curve that is created by plotting the times for culture on the horizontal axis and a logarithmic scale representing the number of cells on the vertical axis. In addition, a culture curve can be created by measuring OD600 nm in a medium. Also, when the expression of the formate dehydrogenase gene is induced, the expression is preferably induced when the growth has passed the logarithmic growth phase and then entered the stationary phase. Here, "stationary phase" refers to a period during which the tangential slope of the above growth curve becomes almost 0.

Also, the optimum temperature for the growth of a host is known to fall within a temperature range that differs depending on host. For example, when an *Escherichia coli* B strain is used as a host, the optimum growth temperature is 37° C. Specifically, when an *Escherichia coli* B strain is used as a host, a temperature range that enables the growth of *E. coli* is between 15° C. and 37° C. Therefore, when the *Escherichia coli* B strain is used as a host, a range of temperatures that are lower than the optimum temperature for the growth of the host and allow the survival of the host is a temperature range between 15° C. and 37° C. In particular, when the *Escherichia coli* B strain is used as a host, when the growth has passed the logarithmic growth phase, culture is preferably continued at a culture temperature of about 20° C.

The above temperature range is employed when the growth of the host has passed the logarithmic growth phase, so that the formate dehydrogenase gene is expressed and formate dehydrogenase exhibiting very high specific activity is generated within the host. After culture, the target formate dehydrogenase is produced within the host. Microorganisms or cells are then disrupted and then a crude enzyme suspension is prepared. The crude enzyme suspension contains the formate dehydrogenase exhibiting very high specific activity. Therefore, the thus obtained crude enzyme suspension can be directly used. In addition, the formate dehydrogenase can also be isolated and purified from the thus obtained crude enzyme suspension. At this time, general biochemical methods to be employed for protein isolation and purification can be used independently or appropriately in combination, such as ammonium sulfate precipitation, gel chromatography, ion exchange chromatography, and affinity chromatography. The thus isolated and purified formate dehydrogenase can be used in a form suspended in a buffer or the like with predetermined pH.

Utilization Form of Mutant Formate Dehydrogenase

The above explained mutant formate dehydrogenase exhibits durability significantly higher than that of formate dehydrogenase before mutagenesis, so that it can be used in any reaction system as a good alternative for conventionally known formate dehydrogenase used therein. An example of a utilization form of the mutant formate dehydrogenase is an NADH regeneration system. NADH is used in various enzyme reactions and then converted to NAD⁻. NADH is used as a coenzyme when an optical isomer is biologically synthesized in the fields of chemical industry and pharmaceutical industry, for example. The term "NADH regeneration system" refers to a system by which $NAD^+$ remaining in a reaction system is reduced to result in NADH, NADH is recovered, and then NADH is used again in the above enzyme reaction. The above mutant formate dehydrogenase is caused to act on a reaction system containing formic acid and $NAD^+$, so that the $NAD^+$ can be reduced and NADH can be synthesized.

As described above, the mutant formate dehydrogenase is used for the NADH regeneration system, so that NADH can be efficiently produced from $NAD^+$ contained in the reaction system. In particular, the mutant formate dehydrogenase exhibits durability significantly better than that of conventionally known formate dehydrogenase. Moreover, the mutant formate dehydrogenase can maintain high activity for a period longer than formate dehydrogenase before mutagenesis. Accordingly, through the use of the mutant formate dehydrogenase, NADH productivity can be significantly improved compared with a case in which conventionally known formate dehydrogenase is used.

EXAMPLES

The present invention is hereafter described in greater detail with reference to the following examples, although the technical scope of the present invention is not limited thereto.

Example 1

In this Example, cloning of a *Fusarium*-derived formate dehydrogenase gene was performed, random mutations were introduced into the gene, and then the durability and specific activity of the thus obtained formate dehydrogenase derived from the mutated genes were evaluated.

(1) Reagents

Reagents used herein were produced by NACALAI TESQUE, INC., unless otherwise specified.
Potassium phosphate buffer (KPB) pH 7.5
<Solution A> 0.5 M $KH_2PO_4$ 13.6 g/200 ml
<Solution B> 0.5 M $K_2HPO_4$ 26.13 g/300 ml
0.5 M KPB (pH 7.5) was prepared by mixing Solution A with Solution B in the following proportion.
[Solution A 16 ml]+[Solution B 84 ml]→100 ml
EcoPro T7 system (Novagen)
Lysate, Methionine
1.62 M sodium formate (formic acid Na)
0.5 M KPB (5.5 g/50 ml, pH 7.5) was prepared and then sterilized with a 0.22-μm filter (Millipore).
16.2 mM NAD
0.5 M KPB (581 mg/50 ml, pH 7.5) was prepared and then sterilized with a 0.22-μm filter (Millipore).
mPMS (DOJINDO)
Methoxy PMS was prepared to 0.5 mg/ml with distilled water.
WST1 (DOJINDO)
WST1 was prepared to 8 mg/ml with distilled water.
PD medium
Potato dextrose broth (24 g/L, Difco) was adjusted to pH 7, autoclaved, and then used.
LB medium
LB Broth (20 g/L, Difco) was autoclaved and then used. Before use thereof, ampicillin (SIGMA) was added to the LB medium to 50 μg/ml.
100 mM $MgCl_2$
$MgCl_2 \cdot 6H_2O$ (2.03 g/100 ml) was autoclaved and then used.
ExTaq Polymerase [5 U/μl] (Takara Bio Inc.)
10× Buffer
KOD-Plus-: KOD-Plus-Polymerase [1 U/μl] (TOYOBO)
25 mM $MgSO_4$ 2 mM dNTP, 10× Buffer
Pyrobest DNA polymerase (Takara Bio Inc.)
Triton X-100
100 mM dATP, dCTP, dGTP, dTTP (Takara Bio Inc.)
RNeasy Plant Mini Kit (QIAGEN)
RNA PCR Kit (Takara Bio Inc.)
MinElute Gel Extraction Kit (QIAGEN)
MinElute PCR Purification Kit (QIAGEN)
BigDyeTerminator v3.1 (ABI)
$dH_2O$: DNase/RNase Free Distilled Water (Invitrogen)
Restriction enzyme Nde I/EcoR I (Takara Bio Inc.)
DNA Ligation kit ver2.1, solution I (Takara Bio Inc.)
JM109 Competent Cells (Takara Bio Inc.)
pET-23b(+) vector (Novagen)
pT7 Blue T-vector (Novagen)
KOD-Plus-Mutagenesis Kit (TOYOBO)

(2) Cloning of *Gibberella Zeae* FDH Gene
(2-1) Microbial Strain

A strain (NBRC No. 4474) of *Gibberella zeae* preserved at the NITE Biological Resource Center (hereinafter, referred to as NBRC), which is a related organization of the Incorporated Administrative Agency, National Institute of Technology (NITE) was purchased, regenerated by a specified method, and then cultured using a PD (Potato Dextrose) medium.

(2-2) Isolation of Formate Dehydrogenase Gene
(2-2-1) Amplification of Formate Dehydrogenase Gene Cells obtained by culturing according to the method in 2-1 were prepared using an RNeasy Plant Mini Kit (QIAGEN), so that total RNA (containing mRNA, rRNA, tRNA, and the like) was prepared. First, cDNA synthesis was performed using an RNA PCR Kit (Takara Bio Inc.) and total RNA as a template. Table 1 shows the composition of the reaction solution.

TABLE 1

| (Composition of reaction solution) | |
|---|---|
| Final concentration | |
| 5 mM | $MgCl_2$ |
| 1X | RT buffer |
| 1 mM | dNTP mixture |
| 0.5U | RNase Inhibitor |
| 0.25U | AMV Reverse Transcriptase XL |
| 0.125 μM | Oligo dT-Adpoter primer |
| 5 μg | Total RNA |

RNase free $H_2O$ was added, so that the liquid volume was 10 μl.

A cDNA synthesis reaction was performed using the reaction solution with the above composition and a reaction cycle of 50° C. for 2 hours, 99° C. for 5 minutes, and then 4° C.

Next, PCR was performed using the thus synthesized cDNA as a template and Pyrobest DNA polymerase. Table 2 shows the composition of components in 50 μl of the reaction solution.

TABLE 2

| (Composition of reaction solution) | |
|---|---|
| 1x | Pyrobest buffer |
| 200 μM | dNTPs mixture |
| 2.5U | Pyrobest DNA polymerase |

TABLE 2-continued (Composition of reaction solution)

| 50 pmol | Primer(forward) |
|---|---|
| 50 pmol | Primer(reverse) |
| 10 μl | cDNA solution |

Sterile water was added, so that the liquid volume was 50 μl.

PCR was performed using the reaction solution with the above composition by, after 95° C. for 1 minute, repeating 25 reaction cycles each consisting of 95° C. for 30 seconds, 60° C. for 30 seconds, and 72° C. for 1 minute, followed by 72° C. for 10 minutes and then 4° C. In addition, Gib FDH1-F-Nde I (forward): CGC CAT ATG GTC AAG GTT CTT GCA GTT C (SEQ ID NO: 13) and Gib FDH1-R (reverse): CTA TTT CTT CTC ACG CTG ACC (SEQ ID NO: 14) were used as a primer pair in this PCR.

(2-2-2) Cloning and Structural Analysis of Formate Dehydrogenase Gene

The sizes of various PCR products obtained were confirmed by agarose gel electrophoresis. A PCR product purified from agarose gel using a MinElute Gel Extraction Kit (QIAGEN) was subcloned (GzFDH/pT7) using a pT7 Blue T-vector (Novagen) and JM109 competent cells (Takara Bio Inc.) (see FIG. 2). The isolated formate dehydrogenase gene sequence was 100% consistent (amino acid level) with the sequence (Genbank No. XP_386303) disclosed in the database.

(2-2-3) Construction of Vector for Expression of Formate Dehydrogenase Gene

The plasmid (FDH/pT7) prepared in 2-2-2 was treated with restriction enzymes Nde I/EcoR I. Table 3 shows the composition of the reaction solution. Treatment with restriction enzymes was performed under reaction conditions of 37° C. for 2 hours.

TABLE 3

(Composition of reaction solution)
Final concentration

| 1X | Universal buffer H |
|---|---|
| 25U | NdeI |
| 25U | EcoRI |
| 5 μg | GzFDH/pT7 |

Sterile water was added, so that the total volume was 20 μl.

The solution after reaction was subjected to 0.8% agarose gel electrophoresis, a formate dehydrogenase gene (about 1.1 kb) excised from the vector as an Nde I/EcoR I fragment was purified using a MinElute Gel Extraction Kit (QIAGEN). Next, a vector pET23b(+) (Novagen) for gene expression was treated with restriction enzymes in a manner similar to that for FDH/pT7. The above formate dehydrogenase gene fragment was introduced to the Nde I/EcoR I site of the pET23b(+) vector using a DNA Ligation kit Ver.2.1 (Takara Bio Inc.). Subcloning (FDH/pET23b(+)) was then performed using JM109 competent cells (Takara Bio Inc.) (see FIG. 2).

(3) Preparation of Mutant Formate Dehydrogenase by Site-directed Mutagenesis (3-1) Multiple Mutant Formate Dehydrogenase Mutations were site-specifically introduced to FDH using a KOD-Plus-Mutagenesis Kit according to the protocols. Table 4 shows the thus prepared mutants and combinations of templates and primers used for preparation. Table 5 shows the sequences of primers used herein.

TABLE 4

| | Prepared plasmid | Site for mutagenesis | Template plasmid | Primer Forward | Primer Reverse |
|---|---|---|---|---|---|
| 1 mutation | 5-O11-B | V99I | WT | 5-O11-B-F | 5-O11-B-R |
| Triple | 3M-4 | V153I/H155Q | 5-O11-B | LoopF-155 | LoopR-153 |
| | 3M-2 | V153I/Q159L | 5-O11-B | LoopF-159 | LoopR-153 |
| Quadruple | 19K-2 | N298Y | 3M-4 | 298NY-F | 298NY-R |
| | 4A-1 | G73A | 3M-2 | 73GA-F | 73GA-R |
| | 15H-5 | G73A | 3M-4 | 73GA-F | 73GA-R |
| | 16F-2 | H287Q | 3M-4 | H287Q-F | H287Q-R |
| | 9M-2 | E60V | 3M-4 | E60V-F | E60V-R |
| Quintuple | 5A-2 | N298Y | 4A-1 | 298NY-F | 298NY-R |
| | 5B-2 | N298Y | 15H-5 | 298NY-F | 298NY-R |
| | 5B-4 | G73A | 16F-2 | 73GA-F | 73GA-R |
| | 5B-5 | N298Y | 16F-2 | 298NY-F | 298NY-R |
| | 5B-6 | G73A | 9M-2 | 73GA-F | 73GA-R |
| | 5B-7 | N298Y | 9M-2 | 298NY-F | 298NY-R |
| | 5C-2 | Q155K | 5B-2 | Q155K-F | 5B-2-155-R |
| Hexatic | 6A-1 | M239L | 5A-2 | 6-O11-B-F | 6-O11-B-R |
| | 6B-1 | M239L | 5B-2 | 6-O11-B-F | 6-O11-B-R |
| | 6B-2 | G73A | 5B-5 | 73GA-F | 73GA-R |
| | 6B-3 | G73A | 5B-7 | 73GA-F | 73GA-R |
| | 6B-4 | H287P | 5B-2 | H287P-F | 286-R |
| | 6B-5 | I31L | 5B-2 | I31L-F | I31L-R |
| | 6B-6 | R50G | 5B-2 | R50G-F | R50G-R |
| | 6B-7 | I136V | 5B-2 | I136V-F | I136V-R |
| | 6B-8 | E293D | 5B-2 | E293D-F | E293D-R |
| | 6B-9 | N343R | 5B-2 | N343R-F | N343R-R |
| | 6B-10 | I64V | 5B-2 | I64V-F | I64V-R |
| | 6B-11 | K82R | 5B-2 | K82R-F | K82R-R |
| | 6B-12 | Q159N | 5B-2 | Q159N-F | 5B-2-155-R |
| | 6C-1 | Q155K | 6B-1 | Q155K-F | 5B-2-155-R |
| | 6C-2 | Q155K | 6B-2 | Q155K-F | 5B-2-155-R |
| | 6D-1 | Q155K/Q159L | 5B-2 | Q155KA156VQ159L-F | 5B-2-155-R |
| Septuple | 7B-1 | D286F/H287P | 5B-2 | D286FH287P-F | 286-R |
| | 7B-2 | D286F/H287Q | 5B-2 | D286FH287Q-F | 286-R |
| | 7B-3 | K82R | 6B-1 | K82R-F | K82R-R |

TABLE 4-continued

| Prepared plasmid | Site for mutagenesis | Template plasmid | Primer Forward | Reverse |
|---|---|---|---|---|
| 7B-4 | K82R | 6B-2 | K82R-F | K82R-R |
| 7D-1 | Q155K/Q159L | 6B-1 | Q155KA156VQ159L-F | 5B-2-155-R |
| 7D-2 | Q155K/Q159L | 6B-2 | Q155KA156VQ159L-F | 5B-2-155-R |

TABLE 5

| Primer | Sequence | SEQ ID NO: |
|---|---|---|
| 298NY-F | TACGCCAAGAACAACTGGGGC | SEQ ID NO: 15 |
| 298NY-R | TCGCAGAGGGTGCTCCTTGGGA | SEQ ID NO: 16 |
| 73GA-F | CTTACCTGACCGCTGAGCGTCTG | SEQ ID NO: 17 |
| 73GA-R | CAGGGTGGAAGGGAGTGGTGAT | SEQ ID NO: 18 |
| Q155K-F | AAAGCTGCTAAGCAGGAGTTCGA | SEQ ID NO: 19 |
| 5B-2-155-R | GGCGATGTCCCACTCACCAGCCT | SEQ ID NO: 20 |
| 6-O11-B-F | TTGTTCAACAAGGACCTCATCTCCAA | SEQ ID NO: 21 |
| 6-O11-B-R | ACCCTTGGTCTTCTCGTGGAGAG | SEQ ID NO: 22 |
| H287P-F | GACCCACAGCCCGCTCCCAAGGAGCA | SEQ ID NO: 23 |
| 286-R | CCAGACATCACCACCGTAACCGGCGA | SEQ ID NO: 24 |
| I31L-F | CTCCGCAAGTGGCTCGAGGACCAA | SEQ ID NO: 25 |
| I31L-R | GCCGAGCTCGTTCTCAGTTGTT | SEQ ID NO: 26 |
| R50G-F | GGTGAGGGTTCCAAATTCGACGA | SEQ ID NO: 27 |
| R50G-R | GTCCTTGTCGGAAGTGGTGA | SEQ ID NO: 28 |
| I136V-F | GTCCGCAACTTCGTCCCTGCCCA | SEQ ID NO: 29 |
| I136V-R | GAGGACGAGGATGGTCATGAGA | SEQ ID NO: 30 |
| E293D-F | TCACCCTCTGCGATACGCCAAGA | SEQ ID NO: 31 |
| E293D-R | TCCTTGGGAGCGGGCTGGTGGT | SEQ ID NO: 32 |
| N343R-F | GACCTCACGACCTCATTGTCCACCA | SEQ ID NO: 33 |
| N343R-R | TGTAGTCGTGGCGACCAGACAGGT | SEQ ID NO: 34 |
| I64V-F | GTCATCATCACCACTCCCTTCCA | SEQ ID NO: 35 |
| I64V-R | CTCAGCATCCTCGAGCTCCT | SEQ ID NO: 36 |
| K82R-F | GGGCCAAGAAGCTCAAGCTCGCT | SEQ ID NO: 37 |
| K82R-R | TGGCCAGACGCTCAGCGGTCA | SEQ ID NO: 38 |
| Q155KA156VQ159L-F | AAAGCGGCTAAGCTGGAGTTCGACCTTGA | SEQ ID NO: 39 |
| 5-O11-B-F | ATCGACCTCAACGCTGCCAACAAGAC | SEQ ID NO: 40 |
| 5-O11-B-R | GTGGTCGGAGCCGATACCAGCGGTA | SEQ ID NO: 41 |
| LoopF-155 | aGCTGCTAAGCAGGAGTTCGACCTTGAG | SEQ ID NO: 42 |
| H287Q-F | ACAGCCCGCTCCCAAGGAGCA | SEQ ID NO: 43 |
| H287Q-R | TGGTCCCAGACATCACCACCGT | SEQ ID NO: 44 |
| E60V-F | TGGATGCTGAGATCATCATCACCA | SEQ ID NO: 45 |
| E60V-R | CGAGCTCCTCGTCGAATTGGAA | SEQ ID NO: 46 |
| Q159N-F | CAAGCTGCTAAGAATGAGTTCGACCTTGA | SEQ ID NO: 47 |

TABLE 5-continued

| Primer | Sequence | SEQ ID NO: |
|---|---|---|
| D286FH287P-F | TTCCCACAGCCCGCTCCCAAGGAGCA | SEQ ID NO: 48 |
| D286FH287Q-F | TTCCAACAGCCCGCTCCCAAGGAGCA | SEQ ID NO: 49 |

In addition, "WT" in the "Template plasmid" column in Table 4 denotes "wild-type FDH." For example, V99I is mutant FDH resulting from substitution of the 99th valine in FDH with isoleucine.

Specifically, an independent mutant formate dehydrogenase gene was first prepared by introducing a V99I mutation into wild-type FDH, and then a V153I/H155Q mutation or a V153I/Q159L mutation were introduced into the gene, so as to prepare a triple mutant formate dehydrogenase gene. An N298Y mutation, a G73A mutation, an H287Q mutation, or an E60V mutation was then introduced into the triple mutant formate dehydrogenase gene, so that a quadruple mutant formate dehydrogenase was prepared.

Of the thus prepared quadruple mutant formate dehydrogenases, 3 types of quadruple mutant formate dehydrogenase genes shown in Table 6 were used for "(4) Evaluation of the properties of recombinant FDH" described later.

TABLE 6

| Plasmid name | Mutation position | | | | | |
|---|---|---|---|---|---|---|
| | 73 | 99 | 153 | 155 | 159 | 298 |
| 19K-2 | | V99I | V153I | H155Q | | N298Y |
| 15H-5 | G73A | V99I | V153I | H155Q | | |
| 4A-1 | G73A | V99I | V153I | | Q159L | |

Also, quintuple-to-septuple mutant formate dehydrogenase genes were similarly prepared. Quintuple-to-septuple mutant formate dehydrogenase genes shown in Table 7 were used for (4) Evaluation of the properties of recombinant FDH described later.

TABLE 7

| Number of mutations | Plasmid name | Mutation position | | | | | | | | |
|---|---|---|---|---|---|---|---|---|---|---|
| | | 31 | 50 | 60 | 64 | 73 | 82 | 99 | 136 | 153 | 155 |
| Quintuple | 5B-2 | | | | | G73A | | V99I | | V153I | H155Q |
| | 5B-4 | | | | | G73A | | V99I | | V153I | H155Q |
| | 5C-2 | | | | | G73A | | V99I | | V153I | Q155K |
| | 5A-2 | | | | | G73A | | V99I | | V153I | |
| | 5B-5 | | | | | | | V99I | | V153I | H155Q |
| | 5B-6 | | | E60V | | G73A | | V99I | | V153I | H155Q |
| | 5B-7 | | | E60V | | | | V99I | | V153I | H155Q |
| Hexatic | 6B-1 | | | | | G73A | | V99I | | V153I | H155Q |
| | 6B-11 | | | | | G73A | K82R | V99I | | V153I | H155Q |
| | 6B-2 | | | | | G73A | | V99I | | V153I | H155Q |
| | 6B-3 | | | E60V | | G73A | | V99I | | V153I | H155Q |
| | 6B-5 | I31L | | | | G73A | | V99I | | V153I | H155Q |
| | 6B-7 | | | | | G73A | | V99I | I136V | V153I | H155Q |
| | 6B-8 | | | | | G73A | | V99I | | V153I | H155Q |
| | 6C-1 | | | | | G73A | | V99I | | V153I | Q155K |
| | 6A-1 | | | | | G73A | | V99I | | V153I | |
| | 6B-4 | | | | | G73A | | V99I | | V153I | H155Q |
| | 6B-6 | | R50G | | | G73A | | V99I | | V153I | H155Q |
| | 6B-9 | | | | | G73A | | V99I | | V153I | H155Q |
| | 6C-2 | | | | | G73A | K82R | V99I | | V153I | Q155K |
| | 6D-1 | | | | | G73A | | V99I | | V153I | Q155K |
| | 6B-10 | | | | I64V | G73A | | V99I | | V153I | H155Q |
| | 6B-12 | | | | | G73A | | V99I | | V153I | H155Q |
| Septuple | 7B-3 | | | | | G73A | K82R | V99I | | V153I | H155Q |
| | 7B-4 | | | | | G73A | K82R | V99I | | V153I | H155Q |
| | 7D-1 | | | | | G73A | | V99I | | V153I | Q155K |
| | 7D-2 | | | | | G73A | | V99I | | V153I | Q155K |
| | 7B-1 | | | | | G73A | | V99I | | V153I | H155Q |
| | 7B-2 | | | | | G73A | | V99I | | V153I | H155Q |

| Number of mutations | Plasmid name | Mutation position | | | | | |
|---|---|---|---|---|---|---|---|
| | | 159 | 239 | 286 | 287 | 293 | 298 | 343 |
| Quintuple | 5B-2 | | | | | | N298Y | |
| | 5B-4 | | | | H287Q | | | |
| | 5C-2 | | | | | | N298Y | |
| | 5A-2 | Q159L | | | | | N298Y | |
| | 5B-5 | | | | H287Q | | N298Y | |
| | 5B-6 | | | | | | | |
| | 5B-7 | | | | | | N298Y | |

TABLE 7-continued

| | | | | | | |
|---|---|---|---|---|---|---|
| Hexatic | 6B-1 | | M239L | | | N298Y |
| | 6B-11 | | | | | N298Y |
| | 6B-2 | | | H287Q | | N298Y |
| | 6B-3 | | | | | N298Y |
| | 6B-5 | | | | | N298Y |
| | 6B-7 | | | | | N298Y |
| | 6B-8 | | | | E293D | N298Y |
| | 6C-1 | | M239L | | | N298Y |
| | 6A-1 | Q159L | M239L | | | N298Y |
| | 6B-4 | | | H287P | | N298Y |
| | 6B-6 | | | | | N298Y |
| | 6B-9 | | | | | N298Y N343R |
| | 6C-2 | | | | | N298Y |
| | 6D-1 | Q159L | | | | N298Y |
| | 6B-10 | | | | | N298Y |
| | 6B-12 | Q159N | | | | N298Y |
| Septuple | 7B-3 | | M239L | | | N298Y |
| | 7B-4 | | | H287Q | | N298Y |
| | 7D-1 | Q159L | M239L | | | N298Y |
| | 7D-2 | Q159L | | H287Q | | N298Y |
| | 7B-1 | | D286F | H287P | | N298Y |
| | 7B-2 | | D286F | H287Q | | N298Y |

(4) Evaluation of the Properties of Recombinant FDH
(4-1) Synthesis of Recombinant FDH by *Escherichia Coli* S30
(4-1-1) Preparation of Template PCR was performed using the plasmids constructed in the previous section (3-1) as templates. The resulting amplification products were used as templates for translation reaction. For PCR, Single-F and Single-R1 were used as a primer pair. The composition of the solution for PCR is shown in Table 8.

```
                                        (SEQ ID NO: 50)
Single-F: 5'-CGA TCC CGC GAA ATT AAT ACG ACT-3'

(SEQ ID NO: 51)
Single-R1: 5'-TCC GGA TAT AGT TCC TCC TTT CAG-3'
```

TABLE 8

| | |
|---|---|
| 10XBuffer | 5 μl |
| dNTP (2mMeach) | 5 μl |
| MgSO₄ (25 mM) | 2 μl |
| Single-F (10 pmol/μl) | 1.5 μl |
| Single-R1 (10 pmol/μl) | 1.5 μl |
| KOD-Plus-DNA Polymerase (1 U/μl) | 1 μl |
| Plasmid DNA | 0.3 μl |
| dH₂O | 33.7 μl |
| | 50 μl |

PCR was performed using a reaction solution with the above composition under conditions of: 94° C. for 2 minutes, and then 30 reaction cycles each consisting of 94° C. for 15 seconds, and 68° C. for 1 minute and 30 seconds, followed by 68° C. for 2 minutes and then 4° C. An about 1.4-kbp fragment amplified by PCR was purified using a MinElute PCR Purification Kit and then used for translation reaction.

(4-1-2) Cell-free Translation Reaction

The translation reaction was performed using the DNA fragment purified in 4-1-1 as a template and an EcoPro T7 system (Novagen). The method was performed according to the protocols for the kit.

(4-2) Evaluation of Durability in S30 (Acceleration Test)

The durability of mutant enzymes in S30 (*Escherichia coli* crude extract) were evaluated with an acceleration test. The procedures are as described below. The translation product prepared in 4-1-2 was dispensed to PCR tubes (1.8 μl each) and then heated with a thermal cycler at 52° C., 56° C., or 57° C. Tubes were removed every 0, 25, and 50 minutes after the initiation of heating and then exposed briefly to and cooled with ice. Subsequently, 98 μl of the resultants were added to each tube containing a reagent for activity measurement with the composition shown in Table 9. The resultants were then heated with a thermal cycler at 37° C. (for about 30 minutes). Tubes were removed and then exposed briefly to ice to stop the reaction.

TABLE 9

| <Reagent for activity measurement> | |
|---|---|
| 1.62M Sodium formate | 10 μl |
| 16.2 mM NAD | 10 μl |
| 100 mM KPB(pH 7.5) | 74.63 μl |
| 0.5 mg/ml mPMS | 0.67 μl |
| 8 mg/ml WST1 | 2.7 μl |

In addition, a formic acid degradation reaction mediated by an FDH catalyst is represented by the following formula.

$$HCOO^- + NAD^+ \rightarrow CO_2 + NADH$$

Methoxy PMS (mPMS), which is an electron transfer substance and WST1, which is an oxidation-reduction coloring indicator (both produced by DOJINDO), were added, so that the reaction proceeds as per the following formula. Hence, measurement of yellow formazan with absorbance at a wavelength of 438 nm enables the determination of the amount of degraded formic acid. In addition, the absorption coefficient of yellow formazan was about 6 times that of NADH, enabling determination with higher sensitivity than that possible with direct measurement of NADH.

$$NADH + mPMS \rightarrow NAD^+ + mPMS \text{ (reduced form)}$$

$$mPMS \text{ (reduced form)} + WST1 \rightarrow mPMS + \text{yellow formazan (37000/M·cm, 438 nm)}$$

Yellow formazan was determined by measurement of absorbance at 430 nm using a plate reader (Spectrafluor Plus: TECAN), so that the activity of FDH having a plurality of amino acid mutations prepared in 4-1-2 could be evaluated.

(4-3) Overexpression and Purification of Recombinant FDH in *Escherichia Coli*

(4-3-1) Expression Induction

G. zeae-derived FDH (wild-type and mutant) was expressed as described below. As microbial strains, an *Escherichia coli* BL21 (DE3) strain prepared by introducing the recombinant plasmid 5B-2 constructed in the previous (3-1) and a strain prepared by introducing wild-type FDH were used. Pre-culture was performed using an LB medium (5 ml) at 37° C. for 22 hours. Cells were inoculated to an LB medium (500 ml), so as to obtain a 1.5% culture solution for pre-culture, and then main culture was performed at 37° C. for 4 hours (O.D.600: 3-). Also, as induction culture for inducing protein expression, IPTG was added to a final concentration of 1 mM, and then culture was performed at 20° C. for 16 hours (O.D.600: 3.5-4.1).

After culture, the culture solution was briefly exposed to ice to cool the solution and then cells were collected. The culture solution was divided into two 500-ml tubes, followed by centrifugation at 5200 rpm for 10 minutes at 4° C. The supernatants were discarded, 60 ml of 10 mM KPB (pH7.5) was added to cells for suspension, 120 ml of the suspension was separated into three disruption tubes only for a 50-ml multibead shocker (Yasui Kikai Corporation), and then centrifugation was performed again at 5600 rpm for 5 minutes at 4° C., so that cells were obtained.

(4-3-2) Disruption of Cells Subjected Expression Induction

Cells obtained in (4-3-1) were disrupted while cooling, so that a crude extract was prepared. After cells were collected, the wet cell weight was measured. 10 mM KPB (pH 7.5) was added in an amount 10 times that of wet cells (10 ml per g of wet cell weight) and 0.1-mm glass beads only for a multibead shocker (Yasui Kikai Corporation) were added in an amount equivalent to that of KPB (10 g per 10 ml of KPB). A multibead shocker (Yasui Kikai Corporation) was used for disruption.

A crude extract was prepared according to the procedures. First, a step that involves shaking at 6000 rpm for 120 seconds and after 60 seconds of interval and shaking again under the same conditions was repeated 3 times. Subsequently, centrifugation was performed at 6000 rpm for 20 minutes at 4° C. and then the supernatant was recovered. Centrifugation was then performed at 6000 rpm for 10 minutes at 4° C. and then the supernatants were filtered using a 0.45-μm filter (Millipore), so that a crude extract was prepared.

(4-3-3) Ion Exchange Column

The crude extract prepared in the above section 4-3-2 was fractionated using a HiTrap Q FF column (5 ml) (GE HEALTHCARE BIOSCIENCE). The procedures are as follows. First, 25 ml of 10 mM KPB (pH 7.5) was supplied to the column at a flow rate of 1 ml/min and then equilibration was performed. Next, the crude extract was supplied at a flow rate of 1 ml/min for binding of protein components. Next, 25 ml of 10 mM KPB (pH 7.5) was supplied to the column at a flow rate of 1 ml/min and then washing was performed. Next, with 10 mM KPB (pH 7.5) as a base, NaCl (10 ml) with a gradient from 0 mM to 200 mM was supplied to the column at a flow rate of 0.5 ml/min, and thus elution was performed. In addition, fractionation was performed so that the amount of each fraction was 0.5 ml. Finally, 15 ml of 10 mM KPB (pH 7.5) and 500 mM NaCl was supplied to the column at a flow rate of 1 ml/min and then washing was performed.

Of fractions obtained by the elution step, fractions for which peaks of FDH activity had been observed were used as samples for secondary purification using a hydroxy apatite column.

(4-3-4) Hydroxy Apatite Column

Secondary purification was performed using the FDH activity-containing fractions obtained in the previous section 4-3-3. The fractions were mixed together to result in a single fraction. The fraction was subjected to 30 minutes of centrifugation using an Amicon Ultra-15 (30 kDa cut) (Millipore) at 5000 rpm and 4° C. After demineralization, the resultant was diluted to about 15 ml with mM KPB (pH 7.2). An Econo-Pac CHT-II column (5 ml) (BIO-RAD) was used for secondary purification. Procedures are as described below.

First, 30 ml of 1 mM KPB (pH 7.2) was supplied to the column at a flow rate of 1 ml/min and then equilibration was performed. After demineralization, a sample was supplied to the column at a flow rate of 0.5 ml/min (circulated twice) for binding of protein components. Next, 10 ml of 1 mM KPB (pH 7.2) was supplied to the column at a flow rate of 1 ml/min, and then washing was performed. Next, 10 ml each of 1 mM to 10 mM KPB (pH 6.8) was supplied to the column at a flow rate of 0.5 ml/min, and then elution was performed. In addition, fractionation (total of 49 fractions) was performed so that the amount of each fraction was 0.5 ml. Finally, 5 ml of 500 mM KPB (pH 6.8) was supplied to the column at a flow rate of 1 ml/min and then washing was performed.

(4-3-5) Measurement of Purified Protein Concentration

Determination of protein concentration after purification was performed by the Bradford method using a Protein Assay reagent. Next, on the basis of this value, wild-type FDH and mutant FDH (5B-2) were each adjusted with 1 mM MOPS (pH7.5) so that the protein concentration of each thereof was 0.067 mg/ml.

(4-4) Measurement of Durability of FDH Mutant

Wild-type FDH and mutant FDH (5B-2) were each adjusted to have a concentration of 0.067 mg/ml. Each of the thus obtained enzyme solutions was dispensed at 5 μl per 0.2-ml tube (BIO-RAD) to 0.7M MOPS (pH 7.5), 10 mg/ml BSA, and 0.3 M trehalose, and then the remaining activity was measured after 500 hours of heating with a thermal cycler (BIO-RAD) at 37° C.

(5) Summary of the Results

Figure 3:
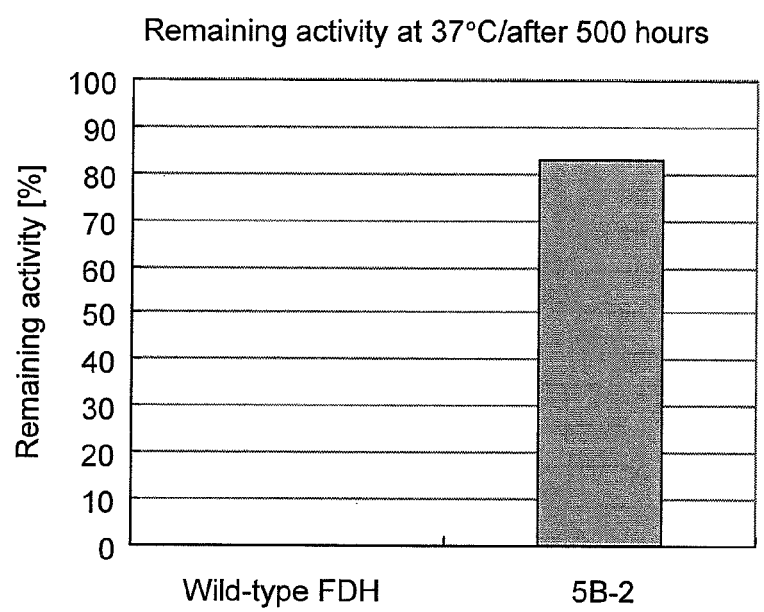
FIG. 3 is a characteristic diagram showing the remaining activity of wild-type FDH and quintuple mutant formate dehydrogenase denoted with the plasmid name "5B-2" at 37° C. after 500 hours.

FIG. 3 shows the results of the durability test performed in (4-4) above. As shown in FIG. 3, it was revealed that the quintuple mutant formate dehydrogenase (G73A, V99I, V153I, H155Q, and N298Y) denoted with the plasmid name "5B-2" could maintain 80% or more activity even after a time period during which the wild-type formate dehydrogenase almost completely lost such activity. As described above, the quintuple mutant formate dehydrogenase denoted with the plasmid name "5B-2" can be said to be an enzyme having extremely high durability.

Figure 4:
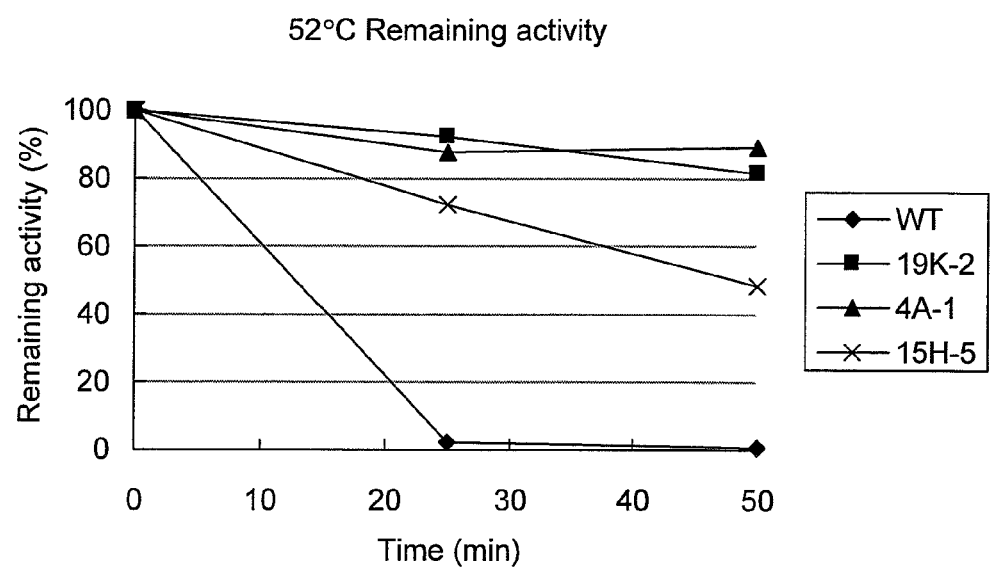
FIG. 4 is a characteristic diagram showing the results of evaluating the remaining activity of quadruple mutant formate dehydrogenase with an acceleration test.
Figure 5:
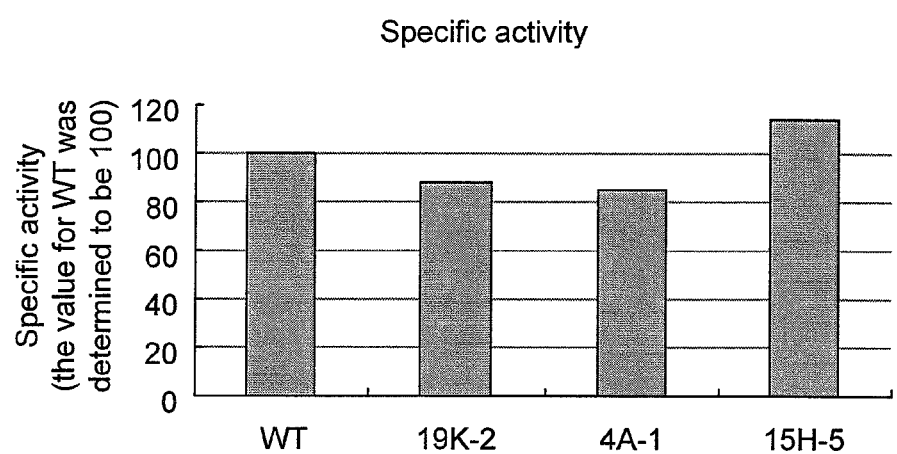
FIG. 5 is a characteristic diagram showing the results of evaluating the remaining activity of mutant formate dehydrogenases prepared in Examples by an acceleration test.
Figure 6:
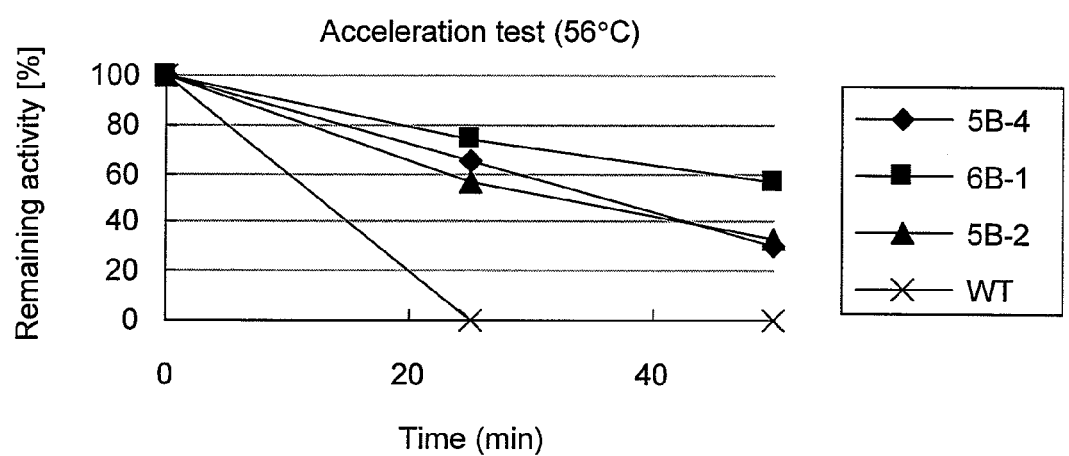
FIG. 6 is a characteristic diagram showing the results of evaluating the remaining activity of mutant formate dehydrogenases prepared in Examples by an acceleration test.
Figure 7:
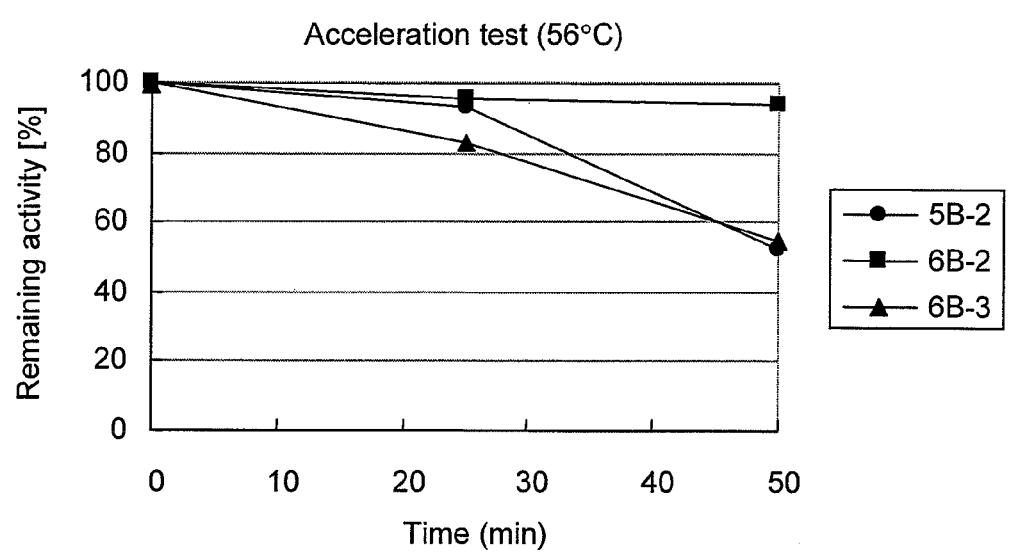
FIG. 7 is a characteristic diagram showing the results of evaluating the remaining activity of mutant formate dehydrogenases prepared in Examples by an acceleration test.
Figure 8:
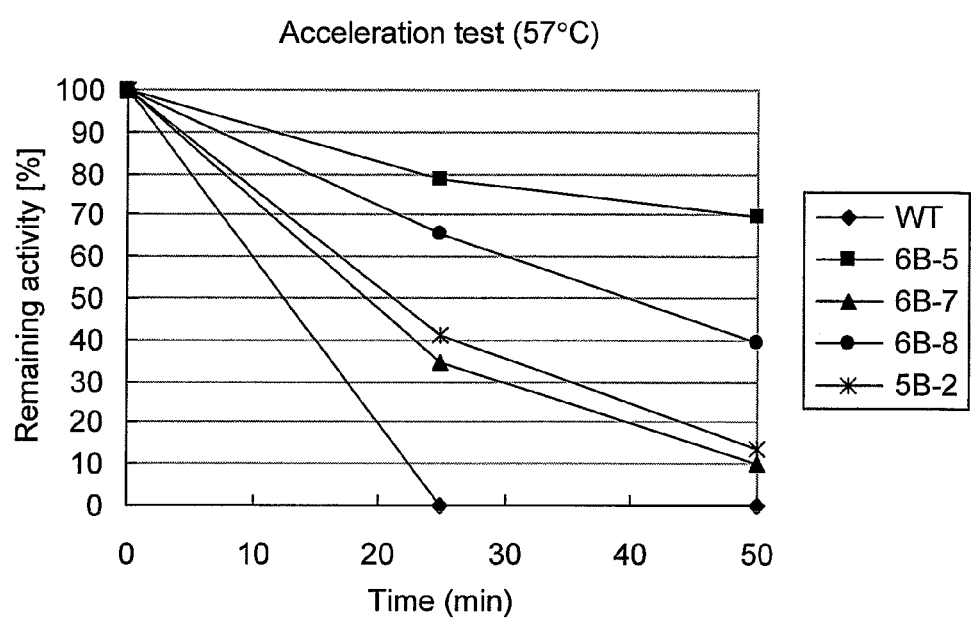
FIG. 8 is a characteristic diagram showing the results of evaluating the remaining activity of mutant formate dehydrogenases prepared in Examples by an acceleration test.
Figure 9:
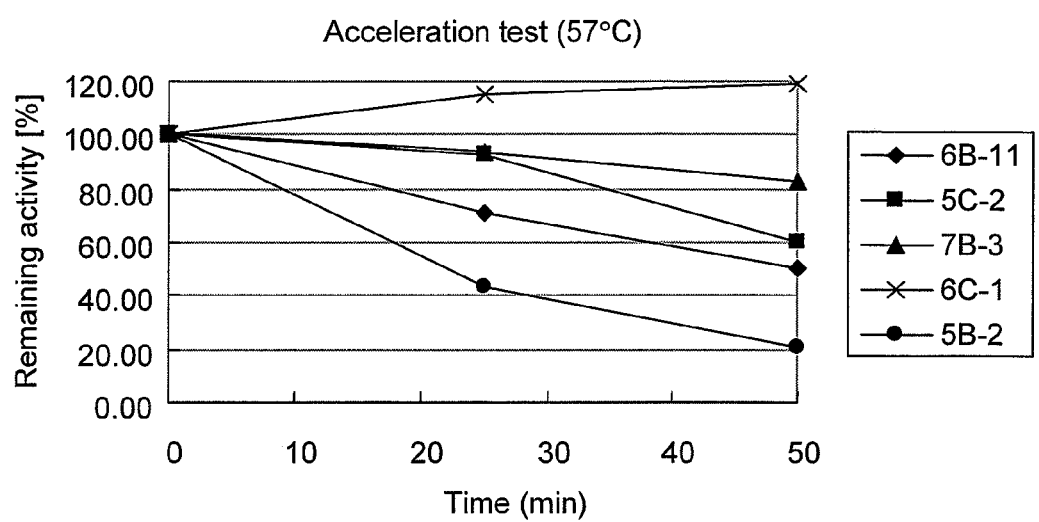
FIG. 9 is a characteristic diagram showing the results of evaluating the remaining activity of mutant formate dehydrogenases prepared in Examples by an acceleration test.

Also, FIG. 4 shows the results of an acceleration test for durability (performed in (4-2) above) for the 3 types of quadruple mutant formate dehydrogenase obtained in (3-1) above. Moreover, FIG. 5 shows the results of measuring specific activity of these 3 types of quadruple mutant formate dehydrogenase and wild-type formate dehydrogenase. As shown in FIG. 5, the 3 types of quadruple mutant formate dehydrogenase obtained in (3-1) above exhibited specific activity almost equivalent to that of the wild-type. In contrast, as shown in FIG. 4, the 3 types of quadruple mutant formate dehydrogenase obtained in (3-1) above were found to have significantly improved durability compared with the wild-type.

FIG. 6 to FIG. 14 show the results of an acceleration test for durability performed for the quintuple mutant formate dehydrogenase, the hexatic mutant formate dehydrogenase, and the septuple mutant formate dehydrogenase obtained in (3-1) above and the wild-type formate dehydrogenase. Also, FIG.

Figure 15:
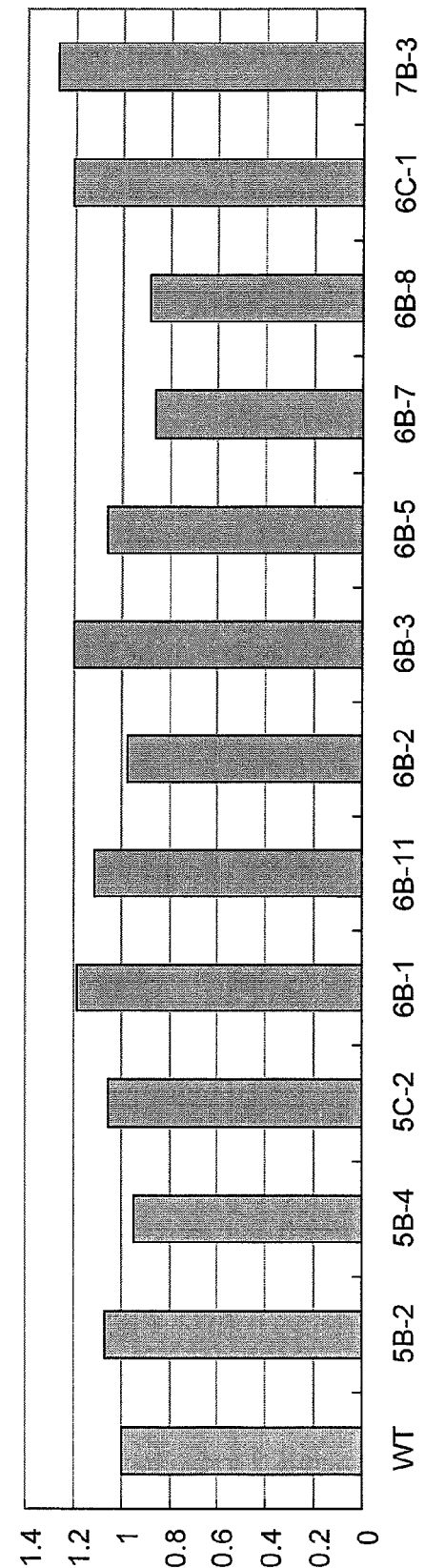
FIG. 15 is a characteristic diagram showing the results of evaluating the specific activity of mutant formate dehydrogenases prepared in Examples.
Figure 16:
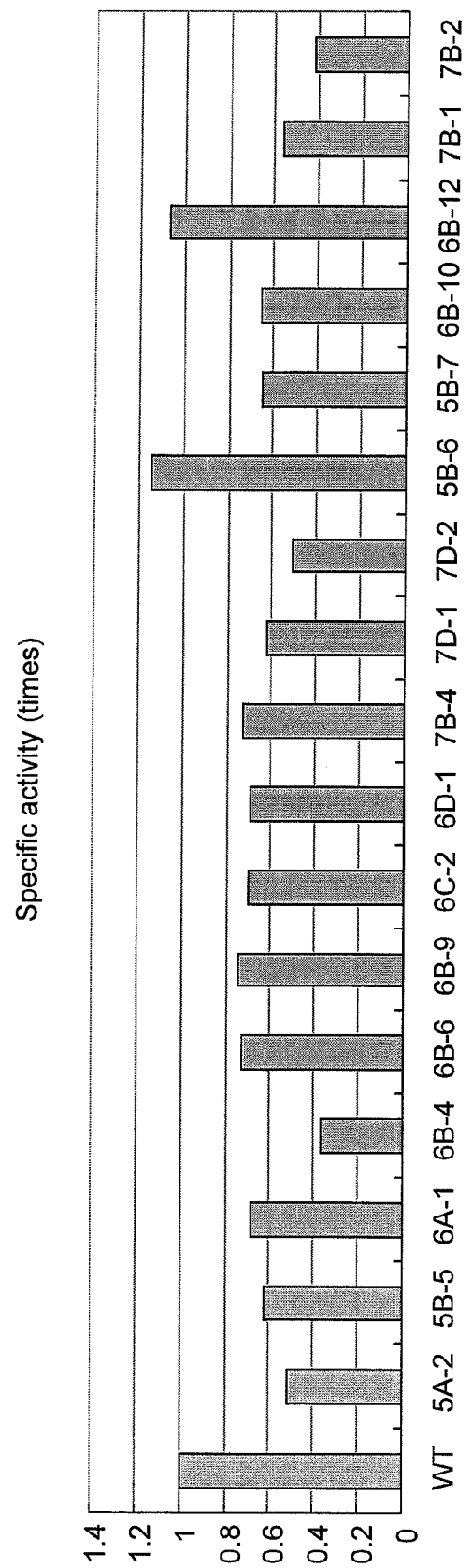
FIG. 16 is a characteristic diagram showing the results of evaluating the specific activity of mutant formate dehydrogenases prepared in Examples.

15 and FIG. 16 show the results of measuring the specific activity of the quintuple mutant formate dehydrogenase, the hexatic mutant formate dehydrogenase, and the septuple mutant formate dehydrogenase obtained in (3-1) above and the wild-type formate dehydrogenase. In addition, FIG. 15 and FIG. 16 show the results as relative values when the specific activity of the wild-type formate dehydrogenase is designated as 1. Also, FIG. 15 shows the results for mutant formate dehydrogenases that exhibited specific activity equivalent to that of the wild-type formate dehydrogenase are shown together. Also, FIG. 16 mainly shows the results of mutant formate dehydrogenases that exhibited specific activity slightly inferior to that of the wild-type formate dehydrogenase.

As shown in FIG. 6 to FIG. 9, it was revealed that the mutant formate dehydrogenases denoted with plasmid names 5B-2, 5B-4, 5C-2, 6B-1, 6B-11, 6B-2, 6B-3, 6B-5, 6B-7, 6B-8, 6C-1, and 7B-3 exhibited good durability while exhibiting specific activity equivalent to that of the wild-type formate dehydrogenase.

Figure 10:
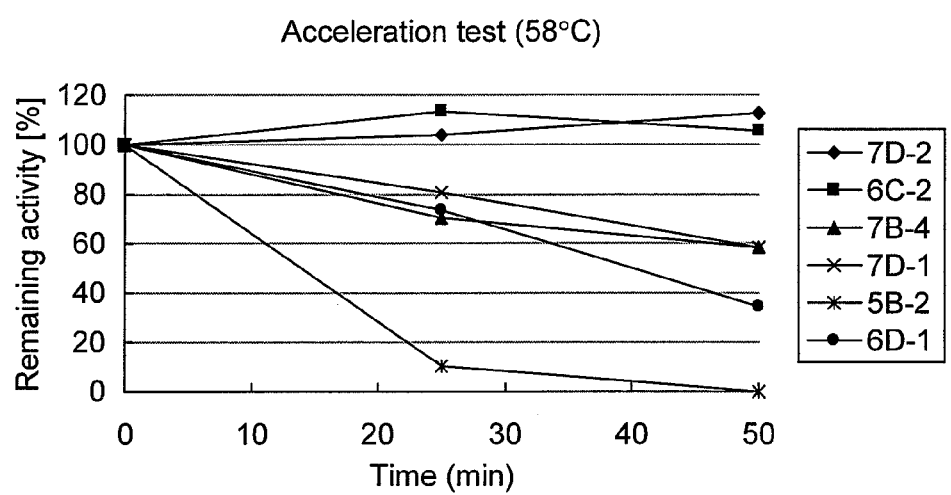
FIG. 10 is a characteristic diagram showing the results of evaluating the remaining activity of mutant formate dehydrogenases prepared in Examples by an acceleration test.
Figure 11:
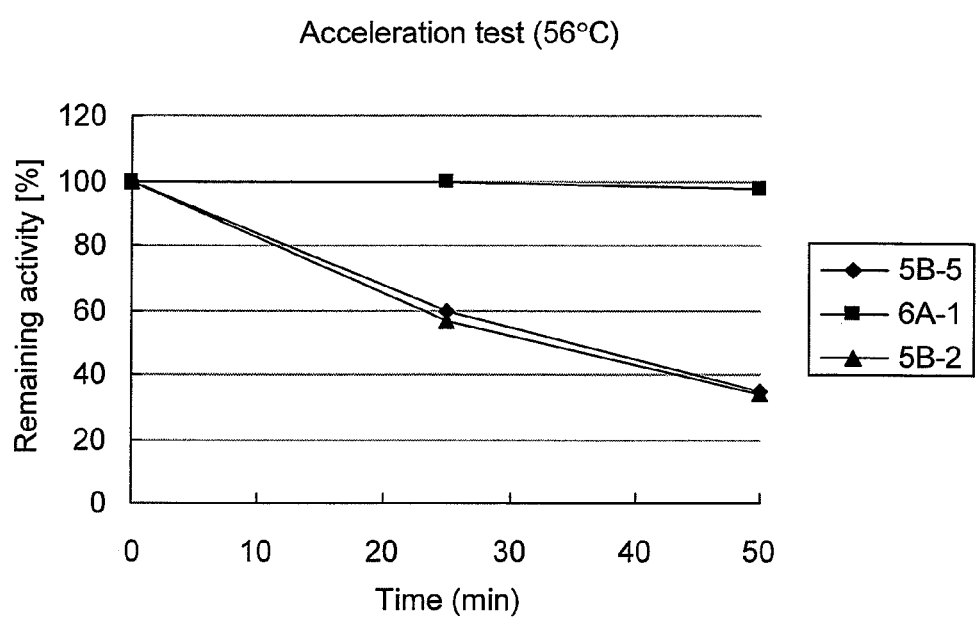
FIG. 11 is a characteristic diagram showing the results of evaluating the remaining activity of mutant formate dehydrogenases prepared in Examples by an acceleration test.
Figure 12:
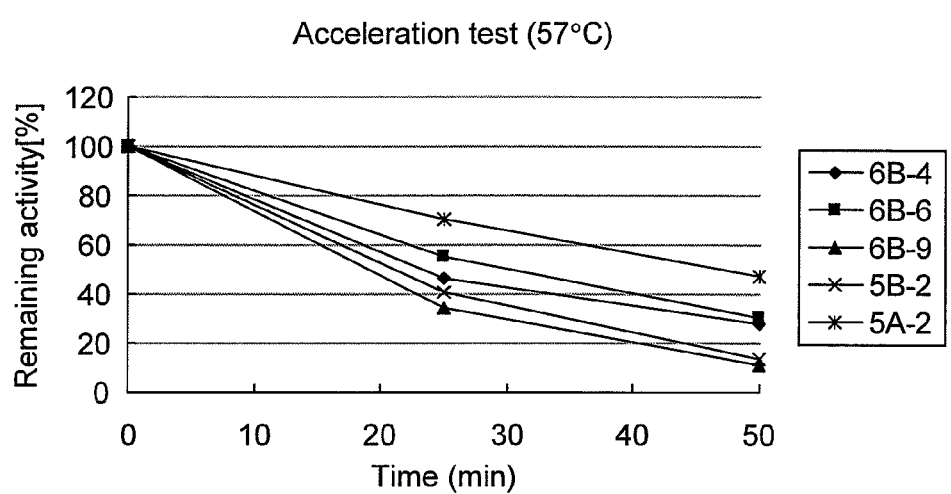
FIG. 12 is a characteristic diagram showing the results of evaluating the remaining activity of mutant formate dehydrogenases prepared in Examples by an acceleration test.

Also, as shown in FIG. 10 to FIG. 12, it was revealed that the mutant formate dehydrogenases denoted with 5A-2, 5B-5, 6A-1, 6B-4, 6B-6, 6B-9, 6C-2, 6D-1, 7B-4, 7D-1, and 7D-2 exhibited good durability while exhibiting specific activity slightly inferior to that of the wild-type formate dehydrogenase.

Figure 13:
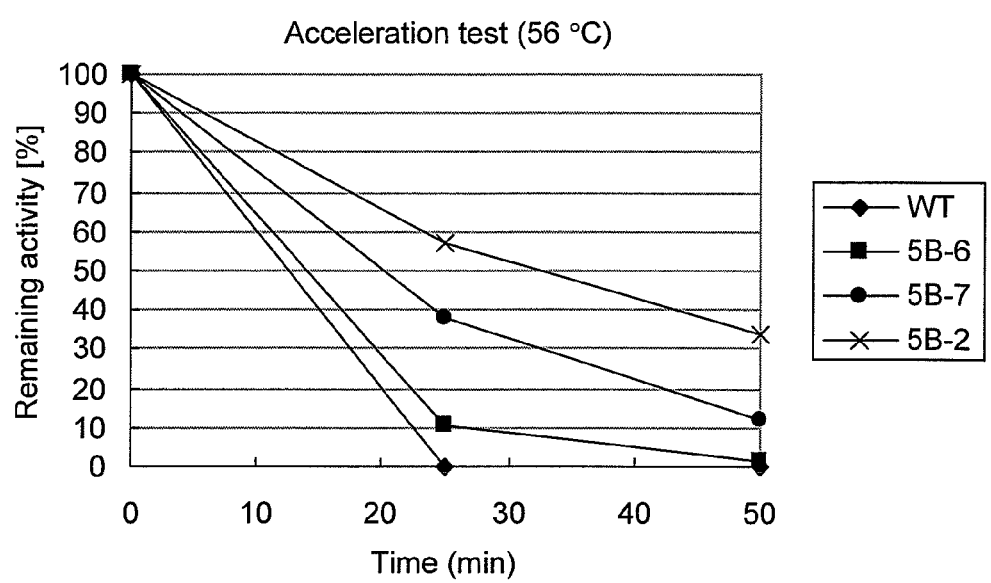
FIG. 13 is a characteristic diagram showing the results of evaluating the remaining activity of mutant formate dehydrogenases prepared in Examples by an acceleration test.
Figure 14:
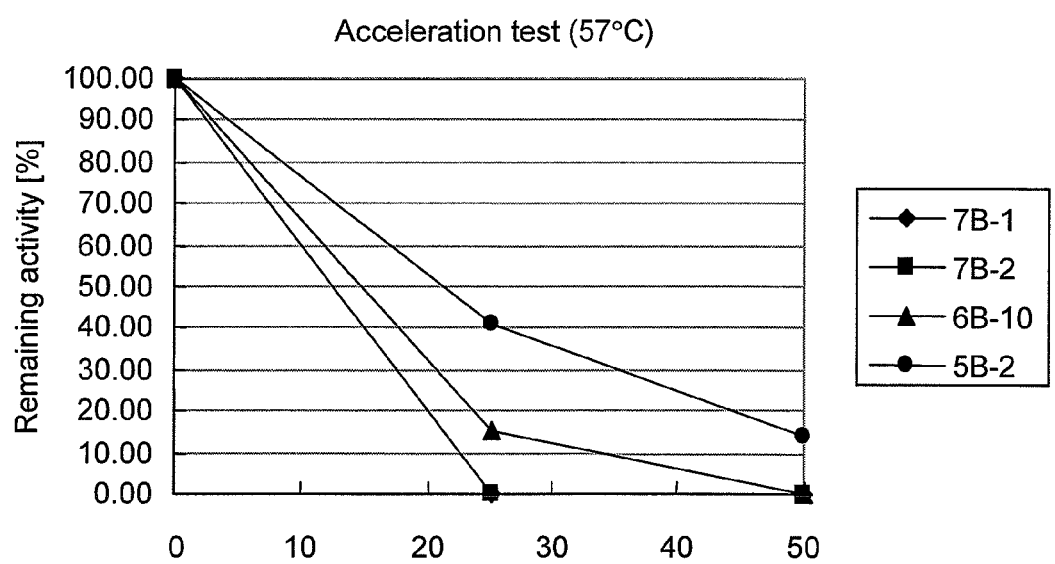
FIG. 14 is a characteristic diagram showing the results of evaluating the remaining activity of mutant formate dehydrogenases prepared in Examples by an acceleration test.

Furthermore, as shown in FIG. 13 and FIG. 14, it was revealed that the mutant formate dehydrogenases denoted with the plasmid names 5B-6, 5B-7, 6B-10, 6B-12, 7B-1, and 7B-2 exhibited higher degrees of durability than the wild-type formate dehydrogenase, although they were inferior to the above mutant formate dehydrogenases in terms of specific activity and/or durability.

Sequence Listing

The invention claimed is:

1. A mutant formate dehydrogenase, having improved durability and comprising any one of the following amino acid sequences:

A) an amino acid sequence having a substitution of the 99$^{th}$ valine with isoleucine, a substitution of the 153$^{rd}$ valine with isoleucine, a substitution of the 155$^{th}$ histidine with glutamine, and a substitution of the 298$^{th}$ asparagine with tyrosine;

B) an amino acid sequence having a substitution of 73$^{rd}$ glycine with alanine, a substitution of the 99$^{th}$ valine with isoleucine, a substitution of the 153$^{rd}$ valine with isoleucine, and a substitution of the 155$^{th}$ histidine with glutamine; and C) an amino acid sequence having a substitution of the 73$^{th}$ glycine with alanine, a substitution of the 99$^{th}$ valine with isoleucine, a substitution of the 153$^{rd}$ valine with isoleucine, and a substitution of the 159$^{th}$ glutamine with leucine;

in the formate dehydrogenase consisting of the amino acid sequence shown in SEQ ID NO: 2.

2. The mutant formate dehydrogenase according to claim 1, further having 1 to 3 substitutional mutations selected from the group consisting of, with respect to the amino acid sequence A):

a substitution of the 31$^{st}$ isoleucine with leucine, a substitution of the 50$^{th}$ arginine with glycine, a substitution of the 60$^{th}$ glutamic acid with valine, a substitution of the 64$^{th}$ isoleucine with valine, a substitution of the 73$^{rd}$ glycine with alanine, a substitution of the 82$^{nd}$ lysine with arginine, a substitution of the 136$^{th}$ isoleucine with valine, a substitution of the 159$^{th}$ glutamine with leucine or asparagine, a substitution of the 239$^{th}$ methionine with leucine, a substitution of the 286$^{th}$ aspartic acid with phenylalanine, a substitution of the 287$^{th}$ histidine with glutamine or proline, a substitution of the 293$^{rd}$ glutamic acid with aspartic acid, and a substitution of the 343$^{rd}$ asparagine with arginine.

3. The mutant formate dehydrogenase according to claim 1, further having 1 to 3 substitutional mutations selected from the group consisting of, with respect to the amino acid sequence B):

a substitution of the 31$^{st}$ isoleucine with leucine, a substitution of the 50$^{th}$ arginine with glycine, a substitution of the 60$^{th}$ glutamic acid with valine, a substitution of the 64$^{th}$ isoleucine with valine, a substitution of the 82$^{nd}$ lysine with arginine, a substitution of the 136$^{th}$ isoleucine with valine, a substitution of the 159$^{th}$ glutamine with leucine or asparagine, a substitution of the 239$^{th}$ methionine with leucine, a substitution of the 286$^{th}$ aspartic acid with phenylalanine, a substitution of the 287$^{th}$ histidine with glutamine or proline, a substitution of the 293$^{rd}$ glutamic acid with aspartic acid, a substitution of the 298$^{th}$ asparagine with tyrosine, and a substitution of the 343$^{rd}$ asparagine with arginine.

4. The mutant formate dehydrogenase according to claim 1, further having 1 to 3 substitutional mutations selected from the group consisting of, with respect to the amino acid sequence C):

a substitution of the 31$^{st}$ isoleucine with leucine, a substitution of the 50$^{th}$ arginine with glycine, a substitution of the 60$^{th}$ glutamic acid with valine, a substitution of the 64$^{th}$ isoleucine with valine, a substitution of the 82$^{nd}$ lysine with arginine, a substitution of the 136$^{th}$ isoleucine with valine, a substitution of the 155$^{th}$ histidine with glutamine or lysine, a substitution of the 239$^{th}$ methionine with leucine, a substitution of the 286$^{th}$ aspartic acid with phenylalanine, a substitution of the 287$^{th}$ histidine with glutamine or proline, a substitution of the 293$^{rd}$ glutamic acid with aspartic acid, a substitution of the 298$^{th}$ asparagine with tyrosine, and a substitution of the 343$^{rd}$ asparagine with arginine.

5. A gene encoding the mutant formate dehydrogenase according to claim 1.

6. A method for producing NADH, comprising contacting the mutant formate dehydrogenase according to claim 1 with a reaction system containing formic acid and NAD$^+$.

* * * * *